US 8,795,606 B2
Aug. 5, 2014

(12) United States Patent
Motadel et al.

(54) INTEGRATED PIPETTE TIP DEVICES

(75) Inventors: Arta Motadel, San Diego, CA (US); Phillip Hairfield, San Diego, CA (US); Peter Paul Blaszcak, San Diego, CA (US)

(73) Assignee: Biotix, Inc., San Diego, CA (US)

( * ) Notice: Subject to any disclaimer, the term of this patent is extended or adjusted under 35 U.S.C. 154(b) by 0 days.

(21) Appl. No.: 13/484,220

(22) Filed: May 30, 2012

(65) Prior Publication Data
US 2013/0323140 A1 Dec. 5, 2013

(51) Int. Cl.
B01L 3/02 (2006.01)

(52) U.S. Cl.
USPC .......................... 422/526; 422/524

(58) Field of Classification Search
USPC ................................. 422/524, 526
See application file for complete search history.

(56) References Cited

U.S. PATENT DOCUMENTS

| | | | |
|---|---|---|---|
| 4,072,330 A | 2/1978 | Brysch | |
| D255,601 S | 6/1980 | De Vaughn | |
| D256,052 S | 7/1980 | De Vaughn | |
| 4,349,109 A * | 9/1982 | Scordato et al. | 206/562 |
| 4,461,328 A * | 7/1984 | Kenney | 141/67 |
| 4,537,231 A | 8/1985 | Hasskamp | |
| 4,565,100 A | 1/1986 | Malinoff et al. | |
| 4,647,419 A | 3/1987 | Helfer et al. | |
| 4,707,337 A | 11/1987 | Jeffs et al. | |
| 4,763,695 A | 8/1988 | Dooley | |
| D300,561 S | 4/1989 | Asa et al. | |
| 5,000,921 A * | 3/1991 | Hanaway et al. | 422/520 |
| 5,032,343 A | 7/1991 | Jeffs et al. | |
| 5,156,811 A | 10/1992 | White | |
| 5,232,669 A | 8/1993 | Pardinas | |
| 5,343,909 A | 9/1994 | Goodman | |
| 5,348,606 A * | 9/1994 | Hanaway et al. | 156/292 |
| 5,487,997 A | 1/1996 | Stolp | |
| 5,614,153 A | 3/1997 | Homberg | |
| 5,660,797 A | 8/1997 | Jarvimaki | |
| D384,418 S | 9/1997 | Torti et al. | |
| 5,700,959 A | 12/1997 | Homberg | |
| 5,827,745 A * | 10/1998 | Astle | 436/54 |
| 5,849,248 A | 12/1998 | Homberg | |
| 6,019,225 A * | 2/2000 | Kalmakis et al. | 206/563 |
| 6,103,198 A | 8/2000 | Brophy et al. | |
| D439,986 S | 4/2001 | Petrek | |
| 6,247,891 B1 | 6/2001 | Lind | |

(Continued)

FOREIGN PATENT DOCUMENTS

EP 0266155 5/1988
EP 0743095 11/1996

(Continued)

OTHER PUBLICATIONS

Apricot Designs Pipette Tips Catalog for EZ-Load Tips, ESP Tips and High Volume Apricot Tips, printed from the internet on Oct. 19, 2011 from http://www.apricotdesigns.com/pipette_tips.htp.

(Continued)

*Primary Examiner* — Jill Warden
*Assistant Examiner* — Brittany Fisher
(74) *Attorney, Agent, or Firm* — Grant IP, Inc.

(57) ABSTRACT

Disclosed herein are fluid handling devices that include integrated card and pipette tip devices, for use with multichannel liquid dispensing devices.

18 Claims, 11 Drawing Sheets

(56) References Cited

U.S. PATENT DOCUMENTS

| | | | |
|---|---|---|---|
| 6,258,324 | B1* | 7/2001 | Yiu .......................... 422/526 |
| D461,904 | S | 8/2002 | Petrek |
| D465,844 | S | 11/2002 | Anderson et al. |
| 6,482,362 | B1* | 11/2002 | Smith ........................ 422/513 |
| 6,566,145 | B2 | 5/2003 | Brewer |
| 6,596,240 | B2 | 7/2003 | Taggart et al. |
| D487,593 | S | 3/2004 | Sama |
| 7,335,337 | B1 | 2/2008 | Smith |
| 7,794,664 | B2 | 9/2010 | Pelletier et al. |
| 8,105,555 | B2 | 1/2012 | Lahti |
| D663,042 | S | 7/2012 | Motadel |
| 8,307,721 | B2 | 11/2012 | Motadel |
| 8,323,585 | B2* | 12/2012 | Heavner .................... 422/500 |
| D679,828 | S | 4/2013 | Motadel et al. |
| D680,226 | S | 4/2013 | Motadel et al. |
| D687,562 | S | 8/2013 | Motadel et al. |
| 2003/0152494 | A1* | 8/2003 | Moritz et al. ............... 422/104 |
| 2003/0156994 | A1* | 8/2003 | Mahler et al. .............. 422/100 |
| 2005/0255005 | A1 | 11/2005 | Motadel |
| 2006/0171851 | A1 | 8/2006 | Motadel |
| 2006/0177352 | A1 | 8/2006 | Ziegmann et al. |
| 2007/0017870 | A1 | 1/2007 | Belov |
| 2007/0231215 | A1 | 10/2007 | Mototsu et al. |
| 2009/0007702 | A1 | 1/2009 | Yiu |
| 2010/0196210 | A1 | 8/2010 | Jungheim et al. |
| 2010/0218622 | A1 | 9/2010 | Motadel |
| 2010/0221151 | A1 | 9/2010 | Motadel et al. |
| 2011/0183433 | A1 | 7/2011 | Motadel |
| 2011/0259443 | A1 | 10/2011 | Preschutti et al. |
| 2011/0300620 | A1* | 12/2011 | Belz et al. ................ 435/287.2 |
| 2013/0164194 | A1 | 6/2013 | Motadel et al. |

FOREIGN PATENT DOCUMENTS

| | | |
|---|---|---|
| EP | 1236030 | 5/2001 |
| EP | 1110613 | 6/2001 |
| EP | 1 884 286 | 2/2008 |
| EP | 2140941 | 1/2010 |
| JP | 08-266913 | 10/1996 |
| RU | 2144158 | 1/2000 |
| WO | WO 01/36933 | 5/2001 |
| WO | WO 2006/093925 | 9/2006 |
| WO | WO 2010/081107 | 7/2010 |
| WO | WO 2011/091308 | 7/2011 |

OTHER PUBLICATIONS

Corning Deck Works Pipette Tips, Product Brochure 2010.

Fluid X, Product page for EZ load pipetting heads printed from the internet on Oct. 19, 2011 from http://www.fluidx.co.uk/html/ez_load_head.html.

Sorenson BioScience, Inc. Liquid Handling Products, VWR 2008 Catalog.

Sorenson low binding aerosol barrier tips, MicroReach Guard, capacity 10ul. Catalog No. Z719390, Sigma-Aldrich Co. 2010 Catalog, Printed from the internet on Sep. 9, 2010.

International Search Report and Written Opinion mailed on: Oct. 28, 2011 in International Application No. PCT/US2011/022129 filed on Jan. 21, 2011 and published as: WO 2011/091308 on: Jul. 28, 2011.

Office Action mailed on: Jul. 11, 2012 in U.S. Appl. No. 12/685,590, filed Jan. 11, 2010.

Office Action mailed on: Jan. 10, 2012 in U.S. Appl. No. 12/685,590, filed Jan. 11, 2010.

Office Action mailed on: May 23, 2012 in Design U.S. Appl. No. 29/354,398, filed Jan. 22, 2010.

Office Action mailed on: Feb. 6, 2012 in Design U.S. Appl. No. 29/354,398, filed Jan. 22, 2010.

Office Action mailed on: Jun. 21, 2011 in Design U.S. Appl. No. 29/354,398, filed Jan. 22, 2010.

Office Action mailed on: Jan. 12, 2011 in Design U.S. Appl. No. 29/354,398, filed Jan. 22, 2010.

Office Action mailed on: Jan. 31, 2011 in Design U.S. Appl. No. 29/354,398, filed Jan. 22, 2010.

Office Action mailed on: Sep. 14, 2010 in Design U.S. Appl. No. 29/354,398, filed Jan. 22, 2010.

International Search Report and Written Opinion mailed on: Aug. 25, 2010 in International Application No. PCT/US2010/020666 filed on Jan. 11, 2010 and published as: WO 10/81107 on: Jul. 15, 2010.

International Preliminary Report on Patentability mailed on: Jul. 21, 2011 in International Application No. PCT/US2010/020666 filed on Jan. 11, 2010 and published as: WO 10/81107 on: Jul. 15, 2010.

International Search Report and Written Opinion mailed on Sep. 4, 2013 in International Application No. PCT/US2013/042915, filed on May 28, 2013.

Office Action mailed on Sep. 13, 2013 in U.S. Appl. No. 13/011,747, filed Jan. 21, 2011 and published as US 2011-0183433 on Jul. 28, 2011.

Office Action mailed on Apr. 5, 2013 in U.S. Appl. No. 13/484,220, filed May 30, 2012.

Office Action mailed on: May 3, 2013 in U.S. Appl. No. 13/773,553, filed Feb. 21, 2013 and published as: US 2013-0164194 on: Jun. 27, 2013.

Office Action mailed on: Dec. 3, 2012 in Design U.S. Appl. No. 29/413,135, filed Feb. 10, 2012.

Office Action mailed on: Dec. 3, 2012 in Design U.S. Appl. No. 29/413,368, filed Feb. 14, 2012.

Office Action mailed on: Feb. 6, 2013 in Design U.S. Appl. No. 29/416,179, filed Mar. 19, 2012.

Office Action mailed on: Mar. 26, 2013 in Design U.S. Appl. No. 29/416,179, filed Mar. 19, 2012.

Office Action mailed on: Jun. 14, 2013 in Design U.S. Appl. No. 29/447,034, filed Feb. 28, 2013.

Office Action mailed on Jan. 14, 2014 in U.S. Appl. No. 13/773,553, filed on Feb. 21, 2013 and published as US 2013-0164194 on Jun. 27, 2013.

Office Action mailed on Apr. 15, 2014 in U.S. Appl. No. 13/011,747, filed on Jan. 21, 2011 and published as US 2011-0183433 on Jul. 28, 2011.

* cited by examiner

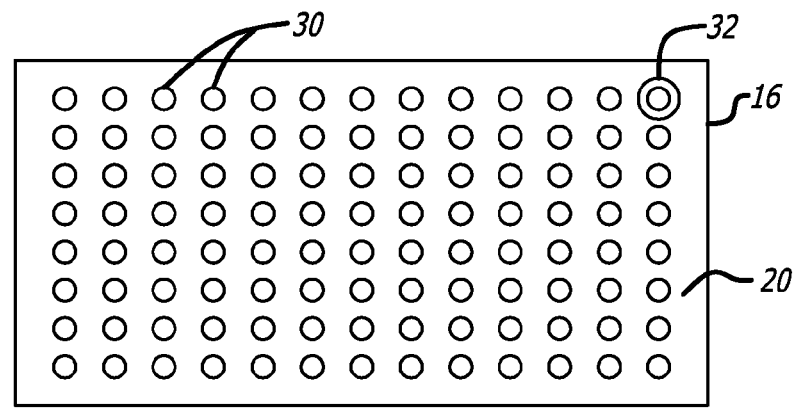
FIG. 1D
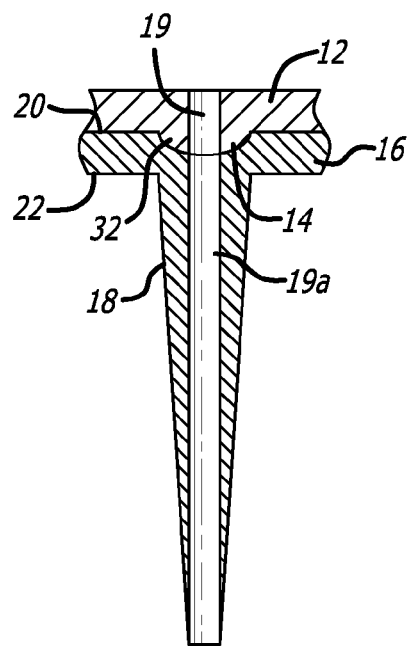
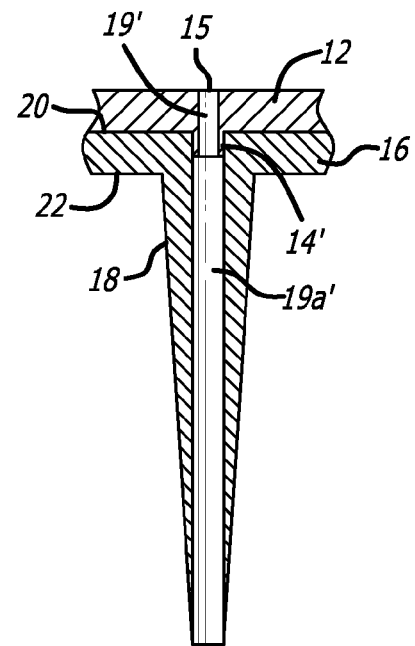
FIG. 1E    FIG. 1F

INTEGRATED PIPETTE TIP DEVICES

FIELD OF THE TECHNOLOGY

The present technology relates in part to pipette tip devices that can be utilized with multichannel liquid dispenser devices.

BACKGROUND

Pipette tips are ubiquitous tools of many research laboratories and of facilities in which small volumes of liquid are handled. Liquid dispensers sometimes are manually operated by a user and sometimes are automated. Liquid dispensing devices often are operated in conjunction with pipette tips, where pipette tips are sealingly connected to the dispensing device, the dispensing device applies negative or positive pressure in the interior of the pipette tips and liquid enters or exits, respectively, the pipette tips.

As laboratory and clinical technologies advance, an increasing number of medical and laboratory procedures are performed by high throughput manual and automated processes. Many of these laboratory or clinical processes and procedures are carried out using pipette tips in conjunction with multichannel dispensing devices (e.g., also known as multichannel pipettors). Multichannel dispensers are currently available with as few as 4 channels (e.g., hand held manually operated pipette) or sometimes as many as 1536 channels (e.g., automated high throughput biological workstations).

Pipette tips generally are held in a tray, rack or holder, and oriented substantially vertically for presentation of the tips for use by an operator. The tips are held in a card of the rack in a vertical orientation such that the proximal portion of the pipette tips can be engaged by the dispenser nozzles or channels. A rack often comprises four sides, and optionally contains a grid structure within the body that confers rigidity to the rack component. Pipette tip racks, available in configurations that can hold from approximately about 96 to about 1536 tips, can be purchased commercially. Each pipette tip often is separated in a rack, and can be utilized individually or in a group of other pipette tips. Pipette tips often are manually loaded into rack or holder devices for sterilization, storage, and ultimate use.

SUMMARY

Provided herein are devices that comprise pipette tips integrated with a card (e.g., co-extensive with, molded or thermoformed to, or connected to a card). These devices are referred to herein as "integrated pipette tip devices."

In certain aspects, provided is a two-piece integrated pipette tip device, including: a card in connection with a plurality of integrated pipette tips and a gasket in sealing connection with a first surface of the card, which card and pipette tips are constructed from a first material and the gasket is constructed from a second material relatively more resilient than the first material; each of which pipette tips includes a distal region and each pipette tip extends from a second surface of the card opposite the first surface; which gasket includes a surface in connection with the first surface of the card, which surface of the gasket covers about 80% or more of the first surface of the card (e.g., about 85%, 90%, 95%, 96%, 97%, 98%, 99%, 100% of the first surface of the card); which card includes card apertures defining channels that traverse the thickness of the card, each of which card apertures is concentric with one pipette tip; and which gasket includes gasket apertures that traverse the thickness of the card, each of which gasket apertures is concentric with one card aperture.

Provided also in some aspects is an integrated pipette tip device, including: a substantially flat card including a first surface and an opposing second surface, which card includes a plurality of apertures, each aperture defining the opening of a channel traversing the thickness of the card; which card includes a plurality of integrated pipette tips, each of which pipette tips including a distal region that effectively extends from the second surface of the card and is concentric with one aperture; and which card includes a plurality of bores, each of which bores having an opening on the first surface of the card located at the intersection of four adjacent apertures, and which bores extend through at least a portion of the thickness of the card.

In certain aspects, also provided is an integrated pipette tip device, including: a substantially flat card including a first surface and an opposing second surface, which card includes a plurality of apertures, each aperture defining the opening of a channel traversing the thickness of the card; which card includes a plurality of integrated pipette tips, each of which pipette tips including a distal region that effectively extends from the second surface of the card and is concentric with one aperture; and which card includes a plurality of dispenser sealing members, each of which sealing members including an opening in effective association with one channel of the card, and each of which sealing members (i) is in connection with the second surface of the card and the distal region of a pipette tip, or (ii) is in effective connection with the first surface of the card and includes one or more sealing member ribs, one or more sealing member depressions, a flange, a flexible material not present in the card or pipette tips, or combination thereof.

Provided in some aspects is an integrated pipette tip device, including: a substantially flat card including a first surface and an opposing second surface, which card includes a plurality of apertures, each aperture defining the opening of a channel traversing the thickness of the card; which card includes a plurality of integrated pipette tips, each of which pipette tips including a distal region that effectively extends from the second surface of the card and is concentric with one aperture; and which card includes a plurality of pipette tip support ribs, each of which pipette tip support ribs is in connection with one pipette tip and the second surface of the card.

In certain aspects, provided is a device provided herein is in sealing connection with a gasket, which gasket includes apertures concentrically aligned with the apertures in the device, which gasket is relatively more resilient than the card of the device, and the surface of the gasket in connection with the first surface of the card covers about 80% or more of the first surface of the card. Provided in some aspects is a method for dispensing a fluid by an integrated pipette tip device, including: engaging a dispensing device with an integrated pipette tip device described herein, drawing a fluid into the pipette tips of the integrated pipette tip device, and dispensing the fluid from the pipette tips. In certain aspects, also provided is a mold configured to manufacture an integrated pipette tip device described herein.

As addressed above, an integrated pipette tip device sometimes includes a sealing member, and a sealing member sometimes is referred to herein as a "collar." A sealing member sometimes is in connection with the first surface or the second surface of the card. A sealing member sometimes is in connection with a pipette tip distal region and often is in effective connection with a channel of the card (e.g., the sealing member is in vacuum connection with a channel). An interior surface of a sealing member sometimes defines a cylindrical or frustrum-shaped void. An interior surface of a pipette tip, e.g., pipette tip distal region, often defines a cylindrical or frustrum-shaped void. An interior surface of a sealing member also sometimes defines a cylindrical or frustrum-shaped void.

Certain embodiments are described further in the following description, claims and drawings.

BRIEF DESCRIPTION OF THE DRAWINGS

The drawings illustrate certain non-limiting embodiments of the technology. For clarity and ease of illustration, drawings are not necessarily to scale, and in some instances, various elements may be shown exaggerated or enlarged to facilitate an understanding of particular embodiments.

FIG. 1D shows a top view of the card portion of a two-piece integrated pipette tip device. FIGS. 1E and 1F show alternate cross-sectional views taken along the line labeled 1E/1F in FIG. 1A. FIGS. 1E and 1F illustrate enlarged views of the internal detail of alternate embodiments of an assembled two-piece device.

FIG. 5A illustrates alternate proximal collar configuration embodiments. FIG. 5C illustrates an embodiment including substantially diamond shaped bores configured to allow increased flexibility of the collar sealing member during dispenser nozzle engagement and disengagement.

DETAILED DESCRIPTION

Figure 1A:
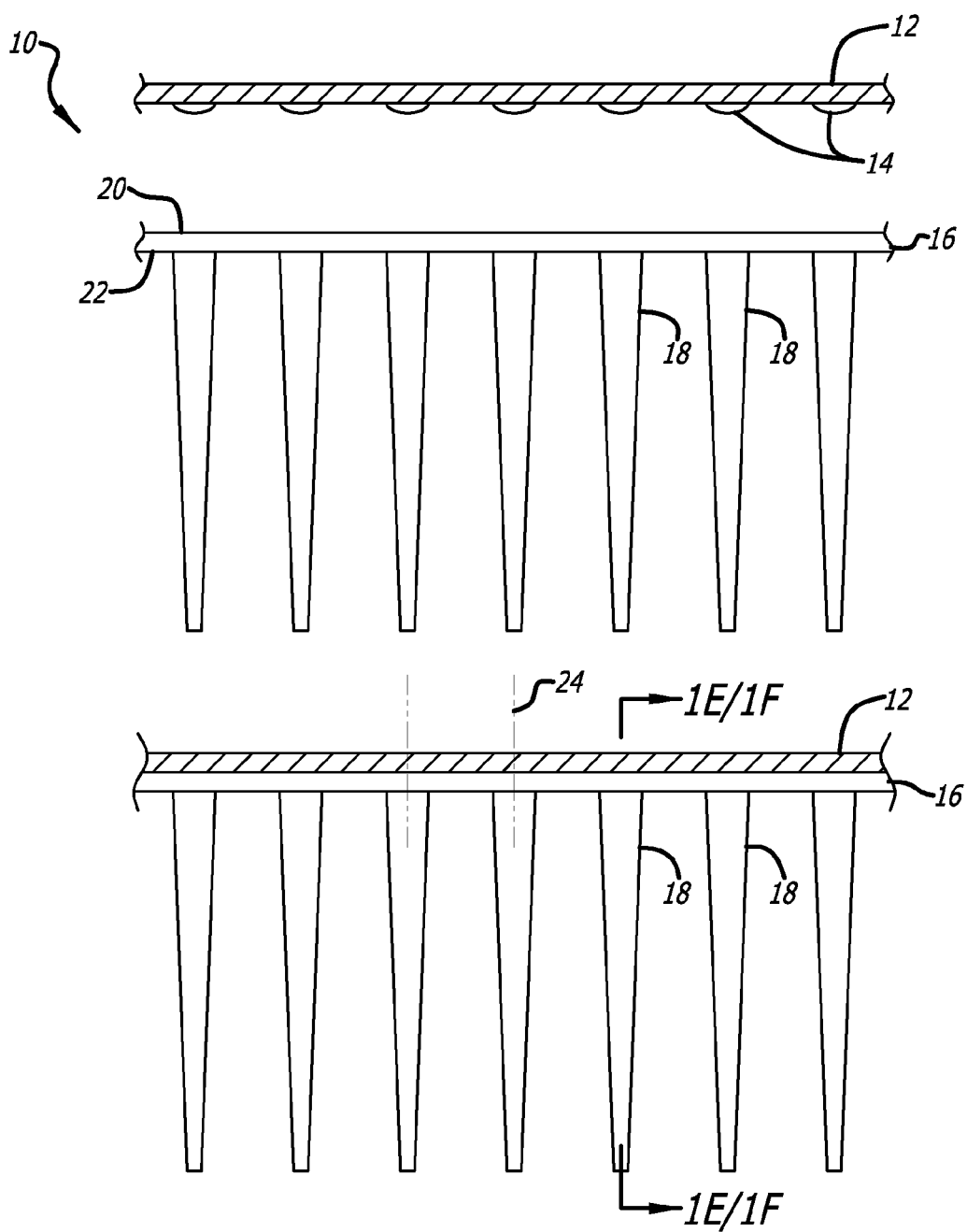
FIG. 1A illustrates exploded and combined profile views of a two-piece integrated pipette tip device.

Laboratories are taking greater advantage of automated and high throughput procedures, and the density of pipette tips utilized in certain applications has increased. For example, multiwell plates often are utilized in high throughput procedures and the plates often are paired with racks having cards that present a number of pipette tips equal to the number of wells in a multiwell plate. For example, where 96 well multiwell plates have been utilized, 384 well plate and 1536 well plate formats presently are in use, which has given rise to pipette tip trays that present 384 and 1536 pipette tips corresponding to the number of wells in the multiwell plates. Pipette tips loaded in 384 tip trays are smaller in size than pipette tips loaded in 96 tip trays, and pipette tips loaded in 1536 tip trays are smaller yet than pipette tips loaded in 384 tip trays. The top surface of a pipette tip rack that holds and presents the pipette tips, which sometimes is referred to as a "card" or "snap plate," generally does not increase in surface area when 96, 384 or 1536 pipette tips are presented, as industry standards regulate and define the length and width dimensions of the rack and snap plate. This limit on snap plate and rack dimensions gives rise to an increased surface density of pipette tips as a greater number of pipette tips are presented by pipette tip racks.

Increased pipette tip density in a rack sometimes can cause an increased frequency of problems with the preparation of and/or used of pipette tips in pipette tip storage racks, including, for example, (i) an increased probability that pipette tips are not perfectly aligned in the racks (e.g., not aligned with an axis perpendicular to the snap plate), which can lead to poor seals when the pipette tips are engaged with a dispensing device and inaccurate and imprecise dispensing volumes; and (ii) an increased effort associated with loading smaller tips, which are more challenging to manipulate, into racks, which can lead to repetitive motion injuries and elevated costs.

Pipette tips also may deviate from substantially vertical alignment in storage boxes due to static charge. Static charge is another challenge that has arisen due to the close packing of smaller, narrower tips in storage units that have remained roughly the same size. As mentioned above, storage units have remained roughly the same size, yet 4 to 16 times as many tips sometimes are stored therein. This significant increase in the number of tips has resulted from the tips being more closely packed, which in turn may allow the tips to make contact with each other in the storage units. The contact between the tips in the storage unit, can lead to the build up of static charge. Due to the tips being constrained in the storage boxes, the static charge can act as a repulsive force between tips in the storage unit. The repulsive force in turn can cause a deviation from vertical alignment of the tips in the storage unit, and thus cause a deviation from concentricity of the pipette tips with respect to the engaging dispenser nozzle. If the tips and nozzles are not substantially axially aligned, the dispenser nozzles may not engage the tips properly, leaving nozzles with improperly engaged pipette tips (e.g., tips that may not seal properly), and, in some instances, no pipette tip at all.

In some instances, electrostatic forces (e.g., static charge) also may be transferred from the pipette tips to a human user handling the tips themselves or with a dispensing device. The static charge also may discharge a shock to samples or specimens the tips come into contact with, which may distort the accuracy of assays being performed. Microscopic specimens, *C. elegans* for example, may be highly affected by the slightest electrostatic force. Additionally, highly sensitive equipment, such as meters, may be effected by static charge and such delicate machinery is oftentimes found in laboratories or settings using multichannel dispensers and pipette tips.

Manual loading of pipette tips into racks and holders represents a bottleneck in the ability to rapidly load tips into holders for preparation, storage and use. In particular, the increase in number of pipette tips, by 4 or 16 times, means 4 or 16 times more repetitive motions (e.g., manual placement of tips in pipette tip holders) per storage unit. Repetitive motion can adversely bear on the health of operators. Increasing the probability of such injuries, coupled with the cost associated with the time-intensive nature of such activities, ultimately drives costs upward for the overall processes.

Integrated pipette tip devices described herein provide advantageous benefits that reduce or eliminate problems associated with (i) loss of concentricity, (ii) static charge build-up, and/or (iii) repetitive motion injuries. Devices presented herein reduce or eliminate difficulties associated with manufacture, loading and storage of pipette tips for multichannel liquid dispensers having 96 or more channels. For example, integrated pipette tip devices described herein reduce or eliminate the loss of concentricity on a central axis shared between the dispenser nozzle and pipette tip proximal portions that the dispenser nozzles engage. Lack of concentricity can be caused by static charge build up in storage units or by shaking or jostling of the storage units. Integrated pipette tip devices reduce or eliminate the loss of concentricity of a shared central axis by constraining the proximal portions of all the tips on a card or plate, and thereby limiting or abrogating lateral movement of the dispenser-engaging openings, in some embodiments.

Integrated pipette tip devices described herein reduce or eliminate deviations in concentricity of upper and lower openings and a central axis by providing reinforcing ribs, in certain embodiments.

In certain embodiments, the reinforcing ribs can prevent (i) lateral movement and pivoting of tips when the tips are engaged with a dispenser, and (ii) pipette tip wall curvature sometimes associated with the manufacture of smaller pipette tips having the thinner walls necessary for use with the thinner dispensers of multichannel dispensers having 96 or more channels. In some embodiments, integrated pipette tip devices also can reduce or eliminate costs associated with potential repetitive motion injury hazards arising from manually loading pipette tips into storage units (e.g., particularly units designed for 384 or 1536 pipette tips), by integrating tips on a card that fits into standard storage units and eliminates the need for individual placement of tips into holders.

Integrated pipette tip devices provided herein (i) stabilize pipette tips, and reduce or prevent lateral movement and/or pivoting of tips when they are engaged with a dispenser; (ii) promote efficient sealing of the pipette tips to a dispenser; (iii) reduce or eliminate the potential for repetitive motion injuries, as multiple pipette tips are loaded in one motion into a rack; (iv) are of relatively simple designs that can be readily manufactured (e.g., injection molded) with relatively small amounts of material; (v) provide pipette tips of substantially regular dimensions and/or geometries; and (vi) reduce or abrogate electrostatic charge that can be generated on or in pipette tips that are not integrated with a card. These features can provide advantageous benefits, including, for example, improved accuracy and precision for liquid volumes delivered by integrated pipette tip devices.

Integrated pipette tip devices can be configured as two-piece or one-piece devices. In general, the card portion (also referred to as a snap plate or pipette tip snap plate) has a substantially similar configuration in one-piece and two-piece integrated pipette tip devices. The card portion often has substantially similar dimensions (e.g., length, width, thickness), can be made of the same materials, and can be manufactured in the same manner, for one-piece and two-piece devices.

Additionally, for cards with similar numbers of pipette tips (e.g., 96, 384, or 1536 pipette tips) the dimensions between tips (e.g., center to center spacing of tips), and the manner in which the tips are arrayed, often are substantially similar between one-piece and two-piece configurations with the same number of tips.

Materials useful for manufacturing devices and components (e.g. moldable plastics, moldable thermoplastic elastomers, anti-static or anti-microbial additives and the like, for example), as well as dimensions of various aspects of the tips (e.g., center to center distances between tips, length of tips, and the like, for example) are described herein. Card members in integrated pipette tip devices can have a thickness between about 0.5 to about 5 milliliters, in certain embodiments. Card members in integrated pipette tip devices can have a thickness about 0.5 millimeters, about 0.6 millimeters, about 0.7 millimeters, about 0.8 millimeters, about 0.9 millimeters, about 1.0 millimeter, about 1.1 millimeters, about 1.2 millimeters, about 1.3 millimeters, about 1.4 millimeters, about 1.5 millimeters, about 1.6 millimeters, about 1.7 millimeters, about 1.8 millimeters, about 1.9 millimeters, about 2.0 millimeters, about 2.1 millimeters, about 2.2 millimeters, about 2.3 millimeters, about 2.4 millimeters, about 2.5 millimeters, about 2.6 millimeters, about 2.7 millimeters, about 2.8 millimeters, about 2.9 millimeters, about 3.0 millimeters, about 3.1 millimeters, about 3.2 millimeters, about 3.3 millimeters, about 3.4 millimeters, about 3.5 millimeters, about 3.6 millimeters, about 3.7 millimeters, about 3.8 millimeters, about 3.9 millimeters, about 4.0 millimeters, about 4.1 millimeters, about 4.2 millimeters, about 4.3 millimeters, about 4.4 millimeters, about 4.5 millimeters, about 4.6 millimeters, about 4.7 millimeters, about 4.8 millimeters, about 4.9 millimeters, or about 5.0 millimeters, in some embodiments.

A pipette tip in devices described herein typically has an upper and lower opening, where the upper opening of a pipette tip proximal opening) may be engaged with a dispensing device, and the lower opening of a pipette tip (distal opening) typically contacts liquid. The upper and lower openings of a pipette tip typically have concentric centers. The terms "concentricity" or "co-centricity", and grammatical variants thereof, as used herein, refers to two or more shapes (e.g., circles, for example) having a common center.

Two-piece devices and methods of use

In some embodiments a two-piece integrated pipette tip device 10 includes an integrated card 16 in connection with a plurality of pipette tips 18 and a gasket 12 in sealing connection with a first surface 20 of the card 16, as illustrated in FIG. 1A. FIG. 1A illustrates two-piece integrated pipette tip device 10, in exploded and assembled views. The card portion of two-piece integrated pipette tip device 10 (and one-piece integrated card devices described below) can also be referred to as a "snap plate", "snap card", "card" or "integrated pipette tip card", throughout the document.

Gasket 12 is configured to be substantially similar in size and shape to the card portion of two-piece card configuration 10. Gasket 12 can be configured to have substantially the same planar shape and surface dimensions as card 16. Gasket 12 can be substantially rectangular in shape, where the length of a side can be between about 120 to about 140 millimeters, and more specifically between about 125 to about 135 millimeters in some embodiments (e.g., about 120 millimeters, about 125 millimeters, about 126 millimeters, about 127 millimeters, about 128 millimeters, about 129 millimeters, about 130 millimeters, about 131 millimeters, about 132 millimeters, about 133 millimeters, about 134 millimeters, about 135 millimeters, or about 140 millimeters). Gasket 12 can range in thickness from about 0.5 to about 3 millimeters (e.g., about 0.5 millimeters, about 0.6 millimeters, about 0.7 millimeters, about 0.8 millimeters, about 0.9 millimeters, about 1.0 millimeter, about 1.1 millimeters, about 1.2 millimeters, about 1.3 millimeters, about 1.4 millimeters, about 1.5 millimeters, about 1.6 millimeters, about 1.7 millimeters, about 1.8 millimeters, about 1.9 millimeters, about 2.0 millimeters, about 2.1 millimeters, about 2.2 millimeters, about 2.3 millimeters, about 2.4 millimeters, about 2.5 millimeters, about 2.6 millimeters, about 2.7 millimeters, about 2.8 millimeters, about 2.9 millimeters, or about 3.0 millimeters).

Figure 1B:
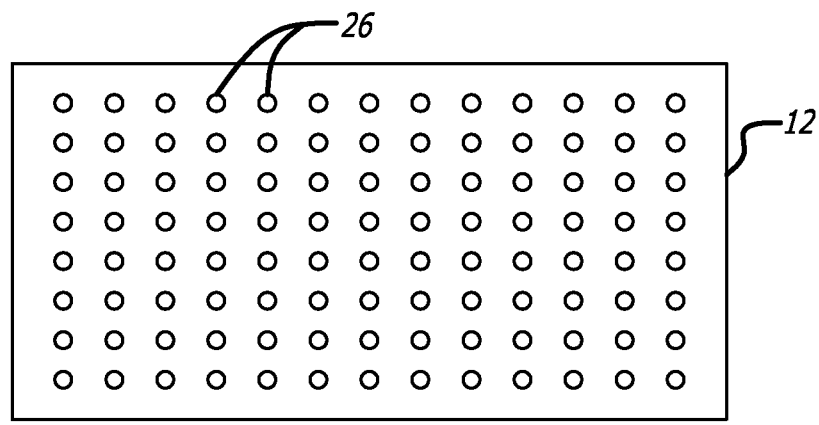
FIG. 1B shows a top view of the gasket portion of a two-piece integrated pipette tip device.
Figure 1C:
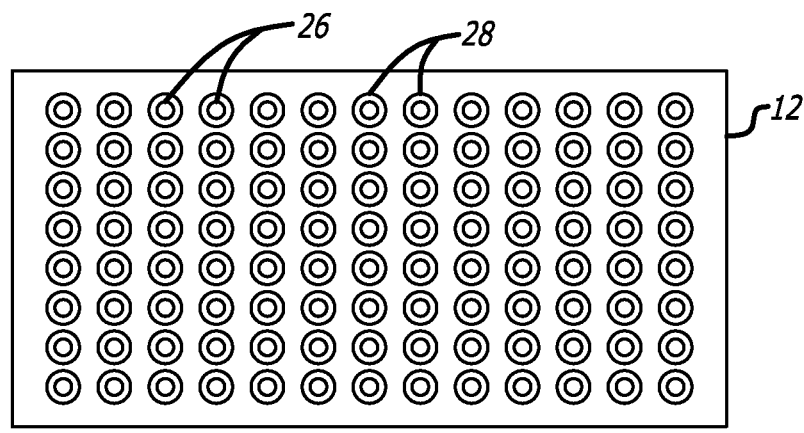
FIG. 1C shows a bottom view of the gasket portion of a two-piece integrated pipette tip device.

The upper surface of a gasket embodiment is illustrated in FIG. 1B. A gasket 12 can have an array of apertures (e.g., openings) 26 that define a channel that traverses the thickness of the gasket. The lower surface of a gasket embodiment is illustrated in FIG. 1O. FIG. 1O shows the bottom of the array of channels terminating in apertures 26. FIG. 1O also shows annular protrusions 28, illustrated as 14 in the profile view presented in FIG. 1A, which are optional.

In some embodiments the lower surface of gasket 12 (FIG. 1O) is in connection with the first surface of card 16, and covers about 80% or more of the first surface of card 16. Gasket 12 covers about 80% or more, about 85% or more, about 90% or more, about 95% or more, or about 100% of the first surface of card 16 in some embodiments. In certain embodiments, gasket 12 may have annular protrusions 14, 14' (see FIGS. 1E and 1F), which protrude from the lower surface of the gasket (e.g., the surface in contact with card 16), and annular protrusions 14, 14' are in contact with the first surface of card 16. The height that annular protrusions 14, 14' (FIGS. 1A) and 28 (FIG. 1O) protrude below the lower surface of gasket 12 can be in the range of about 0.1 to about 1.0 millimeters (e.g., about 0.1 millimeters, about 0.2 millimeters, about 0.3 millimeters, about 0.4 millimeters, about 0.5 millimeters, about 0.6 millimeters, about 0.7 millimeters, about 0.8 millimeters, about 0.9 millimeters, about 1.0 millimeter). In some embodiments, protrusion 14, 14' of gasket 12 is in contact with an inner surface of bore 19' at the interface where gasket 12 and card 16 are in physical contact (see FIG. 1F).

In some embodiments, annular protrusions around apertures in the card, on the top surface of the card (see FIG. 1D), can engage apertures in a gasket (e.g., a gasket having no annular protrusions) and the card. In certain embodiments, annular protrusions around apertures in the card, on the top surface of the card (see FIGS. 2E, 2F, and 3C) can engage a surface of a dispenser nozzle holder and form a seal between the dispenser nozzle holder and the card. In some embodiments the height of the annular protrusions range between about 0.25 millimeters to about 2.0 millimeters in some embodiments (e.g., about 0.25 millimeters, about 0.3 millimeters, about 0.35, 0.4 millimeters, about 0.45 millimeters, about 0.5 millimeters, about 0.6 millimeters, about 0.7 millimeters, about 0.8 millimeters, about 0.9 millimeters, about 1.0 millimeter, about 1.1 millimeters, about 1.2 millimeters, about 1.3 millimeters, about 1.4 millimeters, about 1.5 millimeters, about 1.6 millimeters, about 1.7 millimeters, about 1.8 millimeters, about 1.9 millimeters, or about 2.0 millimeters).

In some embodiments, one, two or more surfaces (e.g., all surfaces) of the gasket may be substantially flat (e.g., the bottom surface of the gasket may be flat and incorporate annular protrusions around apertures). In certain embodiments, gasket 12 can be made from a material that is relatively more resilient than the material used to make devices described herein. In some embodiments, the relatively more resilient material may be a moldable thermoplastic elastomer. In certain embodiments, the relatively more resilient material of the gasket may have absorptive properties.

Figure 5A:
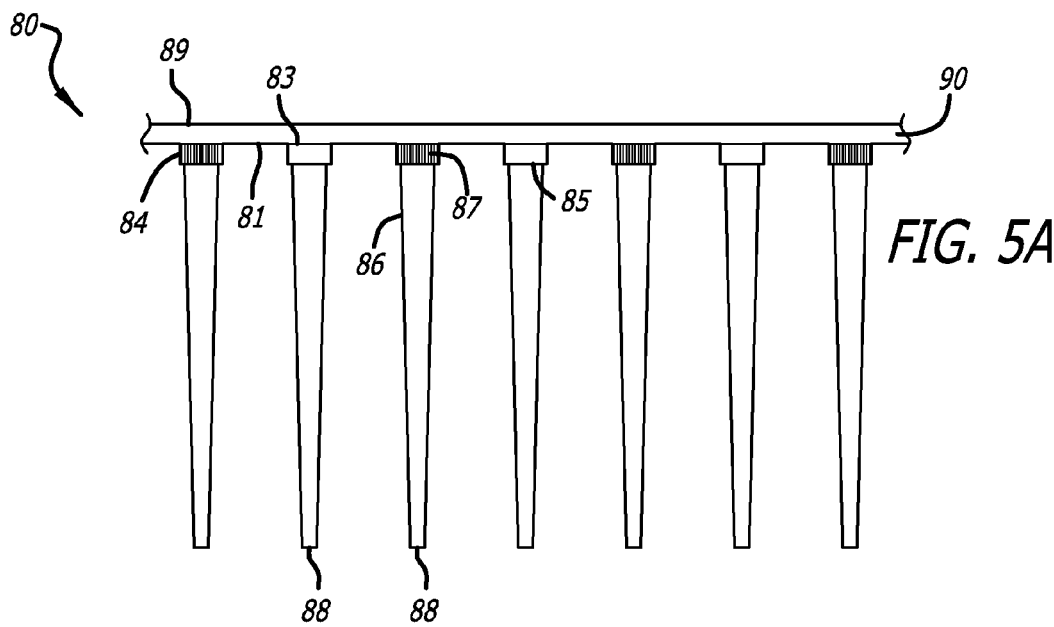
FIG. 5A illustrates a profile view of a one-piece device embodiment having proximal collars, or sealing members, extending from the underside of the card. The tapered or frustum shaped distal portion of each device extends from a proximal collar region.

Integrated card 16 (FIG. 1A), has first and second surfaces, 20 and 22, respectively. The first surface 20 of card 16 also can be referred to as the upper surface while the second surface 22 also can be referred to as the lower surface. The first and second surfaces of the card often are substantially planar in shape and often are substantially parallel to each other. Card 16 is integrated with pipette tips 18. A distal region of each pipette tip 18 can extend from the second surface 22 of card 16, opposite the first surface 20. In some embodiments, each pipette tip 18 extends from a substantially vertical sealing member (e.g., ribbed or non-ribbed dispenser tip engagement zone) that extends from a second surface 81 of card 80, as shown in FIG. 5A. In certain embodiments the sealing member contributes up to ⁄1;3 the total length of the pipette tip extending from a second surface 81 of card 80 (or second surface 22 of card 16). In certain embodiments, the substantially vertical sealing member includes ribs and/or depressions, and in some embodiments the ribs include two or more alternating sets of ribs where each set of ribs has a thickness (e.g., a first thickness, a second thickness, a third thickness, and the like). Ribs may be of the same thickness and length, or of differing thickness and/or length, and sometimes alternate ribs (the next rib) have a different thickness and/or length. Non-limiting examples of ribbed sealing members suitable for use in devices described herein can be found in published U.S. patent application 20110183433, incorporated herein in its entirety by reference.

The upper surface 20 of card 16 is illustrated in FIG. 1D. Card 16 often includes an array of apertures 30, each of which apertures 30 form the opening of a channel that traverses the thickness of the card. In certain embodiments, the channel opening forms a substantially 90 degree edge, or forms a bevel, with surface 20 of the card. In certain embodiments, the aperture includes an edge feature, which often surrounds the aperture. Non-limiting examples of edge-features include a protrusion or depression that transitions to the aperture edge by a surface defined by a right angle, radius, bevel, concave radius, convex radius, the like and combinations thereof. In some embodiments, card 16 may have annular protrusions or depressions 32 extending or recessing from first surface 20, surrounding each of the apertures 30 in card 16. In some embodiments, apertures in the card are surrounded by no protrusion, no depression, a radius, depression, the like, or combination thereof. Apertures, protrusions, depressions and channel cross sections can be of any suitable shape (e.g., circular, annular, ovoid, rectangular, square, rhomboid and the like). Card depression and protrusion embodiments also are shown in FIG. 4A to FIG. 4H.

The apertures in card 16 and apertures in gasket 12 often are concentric (e.g. card aperture 30 is coaxially aligned with gasket aperture 26 (which axis extends through the proximal and distal pipette tip regions), and the apertures often are concentrically aligned with the distal region cross section of each pipette tip 18. In some embodiments, gasket annular protrusions 14, 28 (different views of the same protrusions) surrounding gasket apertures 26, sealingly engage an inner surface of card apertures 30. In certain embodiments card annular protrusions 32 surround card apertures 30 and sealingly engage an inner surface of gasket apertures 26. In certain embodiments, card annular depressions 32 surround card apertures 30 and engage protrusions 14, or like protrusions, in gasket 12. In some embodiments, apertures 30 in card 16 traverse the thickness of the card and can be in connection with the interior volume of a distal region of pipette tips 18. In some embodiments, the reinforcing ribs described below (or the one-piece integrated pipette tip devices described below) can be incorporated in the card piece of two-piece integrated pipette tip devices.

FIGS. 1E and 1F show enlarged views of a single pipette tip from assembled two-piece integrated pipette tip device embodiments. In some embodiments, as illustrated in FIG. 1E, upper surface 20 of card 16 can have depressions concentric with, and configured to be sealingly engaged by, annular protrusion 14, 14' of gasket 12. In some embodiments, a depression 32 in card 16 may facilitate seating and/or sealing of the gasket on the upper surface 20 of the card (e.g., be seating a protrusion 14 of the gasket), and/or can allow proper orientation and subsequent engagement by a dispenser channel. In the embodiment illustrated in FIG. 1E, the central channel 19, through which the dispenser channel enters and engages the two-piece integrated pipette tip device, is illustrated as an opening with a substantially constant diameter from the top to the bottom of the central channel. The channel 19 can align with channel 19a in the pipette tip of card 16. In the embodiment illustrated in FIG. 1F central bore 19' through which the dispenser channel enters and engages the two-piece integrated pipette tip device, is illustrated as an opening in gasket 12 with a first diameter that engages an inner surface of the central channel 19'a of pipette tip 18 that has a second, larger diameter. The channels 19, 19a, 19' and 19a' independently are of any suitable shape and are cylindrical or frustrum shaped in some embodiments.

In certain embodiments, as illustrated in FIG. 1F, upper surface 20 of card 16 can have a substantially flat surface (e.g., no depression in upper surface of card 16), and annular protrusion 14, 14' of gasket 12 can fit within a central bore 19, 19' in card 16 (e.g., illustrated in FIG. 1F). Central bore 15 of aperture 26, and annular protrusion 14' sometimes are configured to align with, and sealingly engage the opening of central bore 19' of card 16'. In the embodiment illustrated in FIG. 1F, the central bore, through which the dispenser channel enters and engages the two-piece integrated pipette tip device (illustrated by the vertical dashed lines in FIG. 1F), is illustrated as an opening with two diameters, where the diameter of bore 15 through gasket 12 is less than the diameter of bore 19' through card 16', and the diameter of opening 15 and annular protrusion 14 can fit within opening 19'. In some embodiments, the diameter of the channel can be the same for the gasket piece and pipette tip-card piece (e.g., as illustrated in FIG. 1E). In some embodiments, the channel diameter can be different for the gasket piece and the pipette tip-card piece (e.g., as illustrated in FIG. 1F). In some embodiments, the upper and lower openings of a gasket piece and/or pipette tip card piece can be (i) connected by tapered or sloped inner pipette tip walls, or (ii) non-tapered or sloped substantially vertical walls. In some embodiments, the upper and lower openings of a gasket piece and/or pipette tip card piece can be connected by tapered or sloped inner pipette tip walls that are co-extensive with substantially vertical dispenser engagement sealing members (e.g., substantially vertical ribbed or non-ribbed collar; see FIG. 5A for non-limiting examples of pipette tips with ribbed and non-ribbed sealing members). In FIGS. 1E and 1F, the central bore openings are of any suitable diameter for the gasket-card engagement and engagement of a dispensing device.

A gasket can be affixed to a card in a two-piece device in any suitable manner. A gasket sometimes is affixed by a friction fit, sometimes is affixed by an adhesive, and sometimes is molded to the card (e.g., in a double-shot molding process). In some embodiments, two-piece integrated pipette tip devices may be used to handle fluids by: engaging a dispensing device; drawing a fluid into pipette tips; emitting the fluid in the pipette tips from the pipette tips. An integrated pipette tip device may be ejected from the dispensing device after the fluid is emitted from the pipette tips, in certain embodiments. In some embodiments the pipette tips of an integrated pipette tip device optionally may be rinsed (e.g., at a washing station of a biological workstation configured with a suitable washing platform).

One-Piece Devices and Methods of Use

Figure 2A:
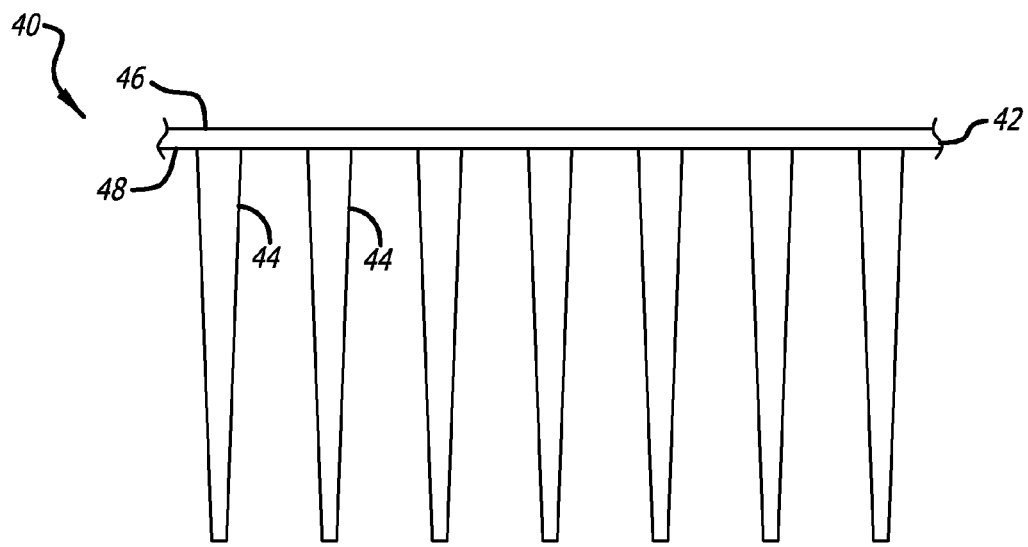
FIG. 2A illustrates a profile view of a one-piece device embodiment.

In some embodiments, an integrated pipette tip device 40 may include a card 42 in connection with a plurality of pipette tips 44, as illustrated in FIG. 2A. Card 42 has a first surface 46 and an opposing second surface 48. As described above for two-piece devices, the first and second surfaces often are substantially planar, and substantially parallel to each other. In some embodiments, first (or upper) surface 46 may be substantially flat.

One-piece integrated pipette tip device 40 also has symmetrical apertures 52 (illustrated in FIG. 2B) traversing the thickness of card 42 and a plurality of pipette tip 44 distal regions can extend from the second surface 48 of the card (illustrated in FIG. 2A). In some embodiments, a plurality of pipette tip 44 distal regions can extend from a plurality of substantially vertical sealing members that can extend from the second surface 48 of card 42 (illustrated in FIG. 2A). In certain embodiments, apertures 52 in card 42 are coaxially aligned and concentric with distal regions of each pipette tip 44. In some embodiments, a dispenser can engage aperture(s) 52 in a one-piece integrated pipette tip device.

Figure 2B:
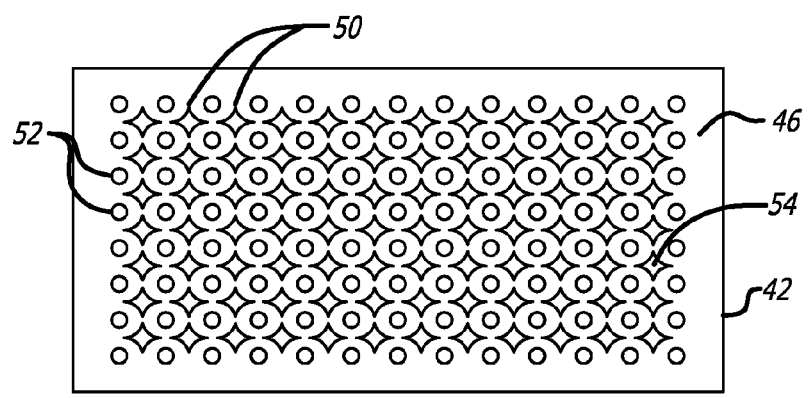
FIG. 2B shows a top view of a one-piece device embodiment illustrating bore or "cutout" regions, which are regions of material thinning or removal in the card portion of the device. Alternate cross-section views of bores or regions of material thinning are illustrated in FIGS. 2C and 2D. Each bore often has an opening on the first surface of the card located at the intersection of four adjacent apertures, which four adjacent apertures often are located at the points of a virtual rectangle or square imaged on the first surface of the card. The center point of such a virtual rectangle or square often is coextensive with the center point of the bore opening.
Figure 2C:
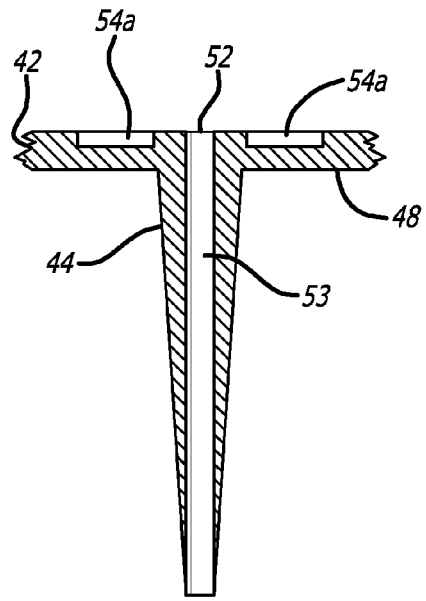
FIG. 2E illustrates an alternate top view of FIG. 2B showing optional annular ring protrusions from the upper surface of the card around the cylindrical apertures of the card.
FIG. 2F illustrates a cross-section view of one of the cylindrical apertures surrounded by a depression in a protruding annular ring shown in FIG. 2E. In certain embodiments, the cylindrical channel of the pipette tip portion is alternatively a tapered channel having a frustum shape that engages a dispensing nozzle of a dispensing device (not shown).
Figure 2D:
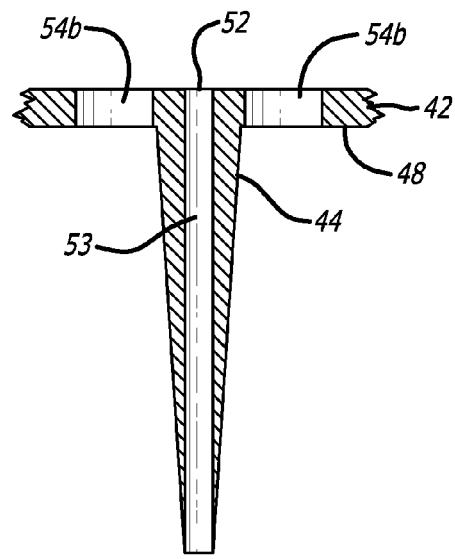
Figure 5B:
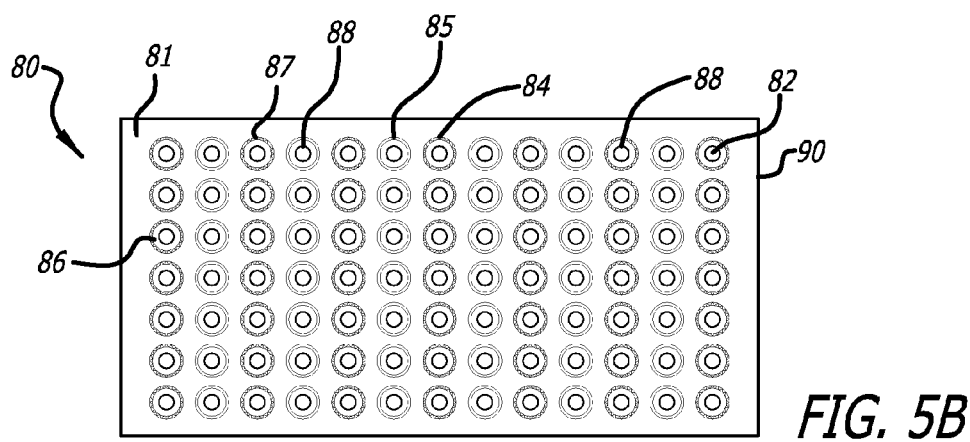
FIGS. 5B and 5C illustrate certain bottom views of the one-piece device embodiments shown in FIG. 5A. The alternate proximal collar embodiments also are shown in FIGS. 5B and 5C.
Figure 5C:
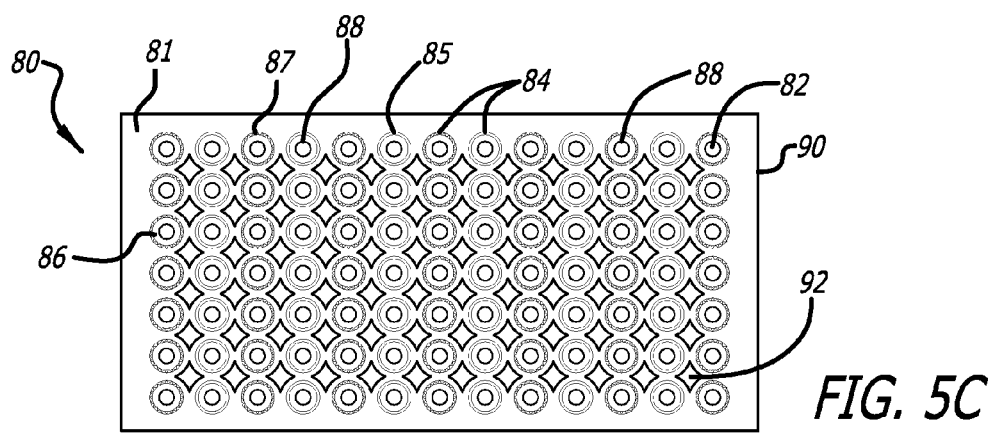

One-piece integrated pipette tip device 40, 80 also may include bores 54, 92 having an opening located on card 42, 90 at the intersection of four apertures 52, 88, in some embodiments (see FIGS. 2B and 5C). In some embodiments, the boundaries of bores 54, 82 are delineated by lines or curves (50 in FIG. 2B) connecting four points located between any four apertures arranged in a two by two (2×2) array. Where four points are drawn on four apertures arranged in a 2×2 array, and the points are connected, the intersection of the diagonal lines connecting the points define the center point of the opening for the bore between the apertures in the 2×2 array. This central opening is shown for bore 54 in FIG. 2B and bore 92 in FIG. 5C. In certain embodiments, bores 54, 92 extend through a portion of the thickness of, or through the entire thickness of, card 42, as shown in FIGS. 2C and 2D. In some embodiments the cross section of bore 54, 92 is substantially square shaped or diamond shaped. A bore may have any other suitable cross-sectional shape, such as a circular, oval or other cross-sectional shape.

FIG. 2C illustrates one embodiment of a bore 54a in which about one third of the card thickness in the bore is removed and configured to enhance card flexibility of the region that engages a dispenser. FIG. 2D illustrates an alternate embodiment of bore 54b in which substantially greater than about 90% of the card thickness is removed to enhance card flexibility (e.g., greater than about 90%, greater than about 91%, greater than about 92%, greater than about 93%, greater than about 94%, greater than about 95%, greater than about 96%, greater than about 97%, greater than about 98%, greater than about 99%, about 100%, or substantially all of the card thickness is removed). In certain embodiments, channel 53 may be cylindrical or frustrum shaped.

The lines or curves defining a bore opening (top view) may be of the same length or of different lengths, in certain embodiments. In some embodiments, the points may be equidistant from each other, with lines or curves (50) of substantially equal lengths or arcs joining the points. In certain embodiments, the points may not be equidistant, and are joined by lines or curves (50), where the lines or curves joining the points may be substantially different lengths or arcs. In some embodiments, each side of the square or diamond is a curved side (50). Bores 54, 92 can allow for movement of plastic in card 42 when the nozzles of a dispensing device engage the apertures 52, 88 of integrated pipette tip device 40, 80, thereby enhancing flexibility of the device in the dispenser sealing zone.

Figure 2E:
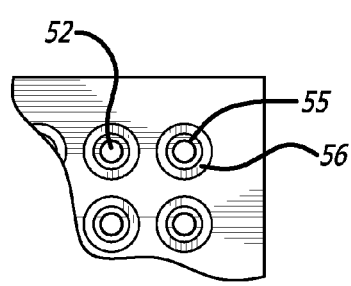
Figure 2F:
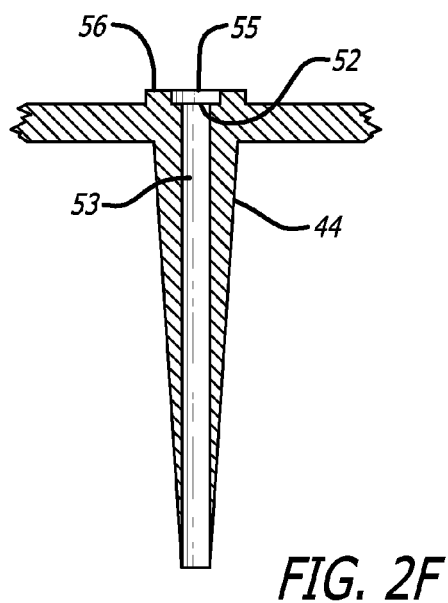

As shown in FIG. 2E, in some embodiments, a one-piece integrated card (e.g., 42, 62, 82) may have annular protrusions and/or depressions extending from first surface 46, 64, surrounding each of the apertures 52. FIG. 2E shows an embodiment in which aperture 52 is surrounded by concentric annular depression 55, which in turn is inset in concentric annular protrusion 56. FIG. 2F shows these features in cross section, and shows channel 53 coextensive with aperture 52. Channel 53 can be cylindrical or frustrum shaped in some embodiments.

Figure 4A:
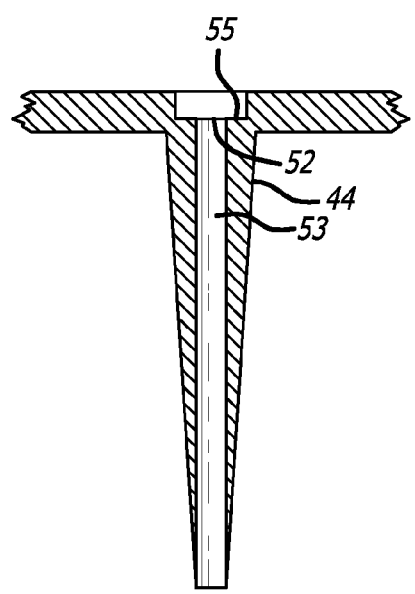
FIG. 4A to FIG. 4G show cross section views of device embodiments having, or configured to incorporate, substantially resilient sealing elements.
Figure 4B:
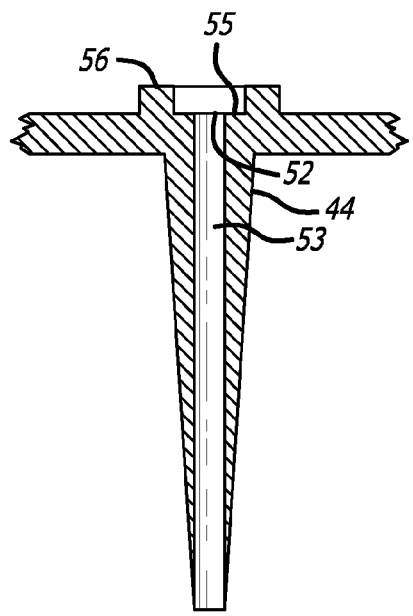
Figure 4C:
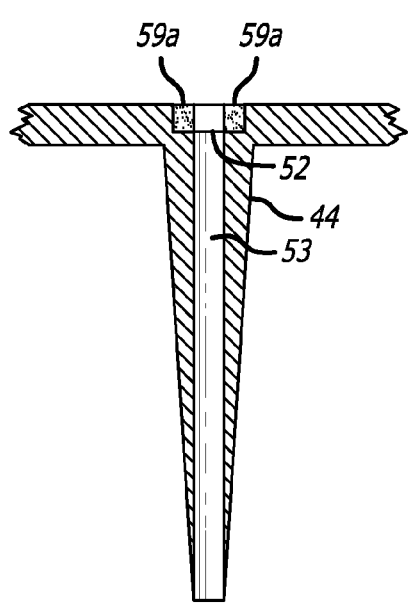
Figure 4D:
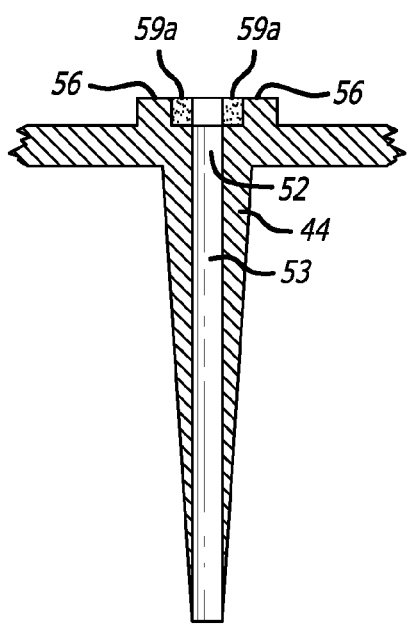
Figure 4E:
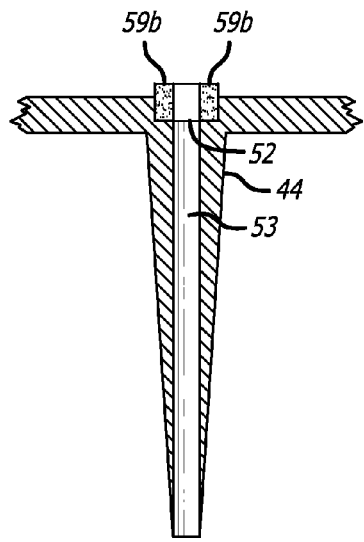
Figure 4F:
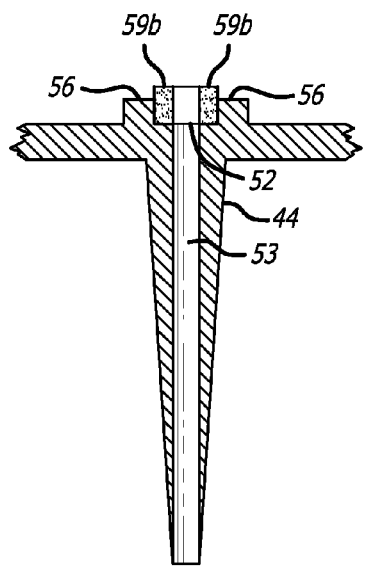
Figure 4G:
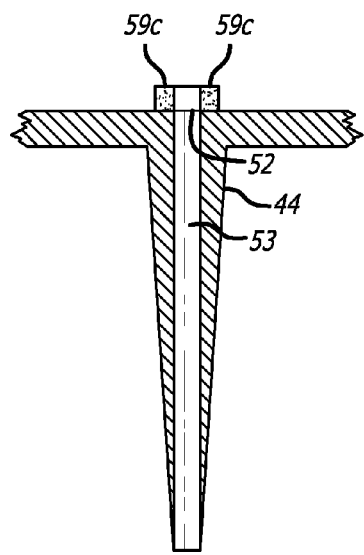
Figure 4H:
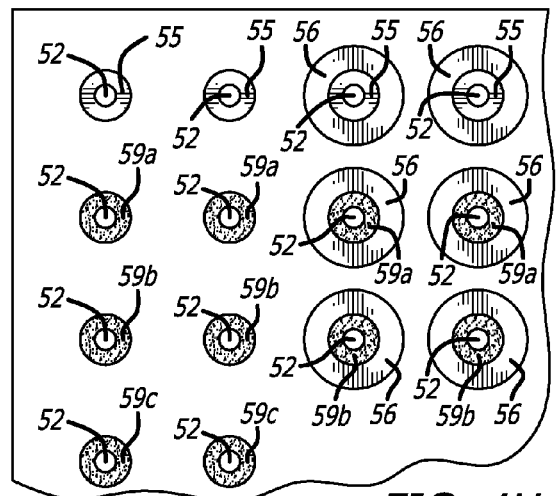
FIG. 4H shows a top view of such device embodiments.

FIG. 4A to FIG. 4G show cross section views of various sealing member embodiments, and configurations for receiving sealing members. FIG. 4A shows a device embodiment that includes an annular depression having depressed surface 55, which depression is depressed from the first surface of the card. The depression is around, and concentric with, circular aperture 52. Channel 53 and the outer surface 44 of a pipette tip distal region are shown. FIG. 4B shows an embodiment in which an annular depression having surface 55 is depressed from surface 56 of a protrusion extending from the first surface of the card. FIG. 4C and FIG. 4D show embodiments in which sealing member 59a is seated in the depression having surface 55, where the top surface of the sealing member is flush or substantially flush with the first surface of the card or surface 56 of the protrusion. FIG. 4E and FIG. 4F show embodiments in which sealing member 59b is seated in the depression having surface 55, where the top surface of the sealing member is proud of or raised above the first surface of the card or surface 56 of the protrusion. FIG. 4G shows an embodiment in which sealing member 59c is deposited on a substantially flat first surface of the card, which card surface includes no depression or protrusion around the aperture. FIG. 4H shows a top view of certain sealing member embodiments shown in FIG. 4A to FIG. 4G. In embodiments shown in FIG. 4A to FIG. 4H, the sealing member often is substantially resilient and often comprises a substantially flexible material (e.g., an elastomer, examples of which are described herein). The sealing member in such embodiments often is more resilient than the pipette tips and card of the device. The sealing member sometimes is a member separate from the device that is pressed into or onto the device, sometimes is retained by a friction fit in the device, and sometimes is retained by an adhesive. The sealing member sometimes is molded onto or into the device, sometimes by a double shot molding process, for example. The sealing member in such embodiments can sealingly engage and disengage a dispenser and promote efficient engagement and disengagement of the integrated pipette tip device and dispenser.

As shown in FIG. 5A, one-piece devices sometimes include a sealing member 84 or 85 (also referred to herein as a collar), having an outer wall that extends in a substantially vertical orientation from the card bottom surface 81. Sometimes the collar is a sealing member 84 having ribs 87 and sometimes the collar is a non-ribbed sealing member 85. A device sometimes includes collars having no ribs, ribs, no depressions, depressions, the like, or a combination thereof. The frustum shaped pipette tip distal portion 86 is co-extensive with a sealing member (e.g., substantially vertically ribbed sealing member 84 or non-ribbed proximal collar sealing member 85). Sealing members (e.g., ribbed dispenser engagement zones, non-ribbed dispenser engagement zones) can be of any configuration suitable for use in devices described herein. In some embodiments, ribbed sealing member walls have an outer surface on which ribs of a first thickness are disposed around the circumference of the walls. The ribs are regularly spaced around the circumference in some embodiments, and sometimes are irregularly spaced around the circumference. In some embodiments, the ribs are uniform (e.g., substantially similar thicknesses, substantially similar widths, substantially similar shapes, substantially similar tapers, the like or combinations thereof), and in certain embodiments, the ribs are non-uniform (e.g., different thicknesses, different widths, different shapes, different tapers, the like or combinations thereof).

Non-limiting examples of ribbed sealing members are known in the art (e.g., U.S. patent application 20110183433, incorporated by reference herein in its entirety).

FIG. 5B shows a bottom view of a one-piece integrated pipette tip device showing ribbed collars 84 and non-ribbed collars 85. FIG. 5C is a bottom view of a one-piece integrated pipette tip device having a bores in which substantially all of the card thickness is removed in the bore. The bores in FIG. 5C may provide flexibility during tip engagement to, and dispensing from, a dispenser. In some embodiments, reinforcing ribs described below can be used in conjunction with integrated pipette tip device 40, 80 (e.g., FIG. 5D, FIG. 5E).

Figure 6A:
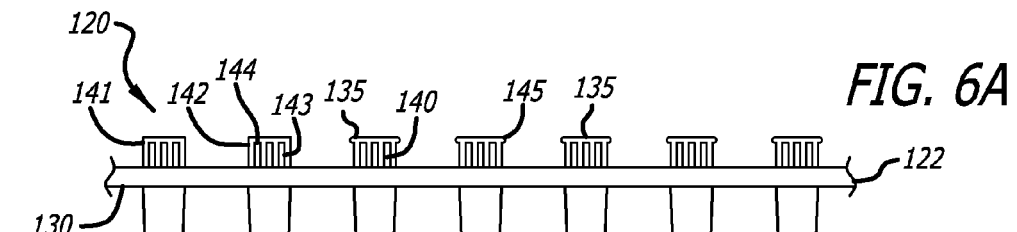
FIG. 6A, FIG. 6B and FIG. 6C show side views of various integrated pipette tip device embodiments that include sealing members comprising ribs and/or depressions, which sealing members are in connection with the first surface of the card.
Figure 6B:
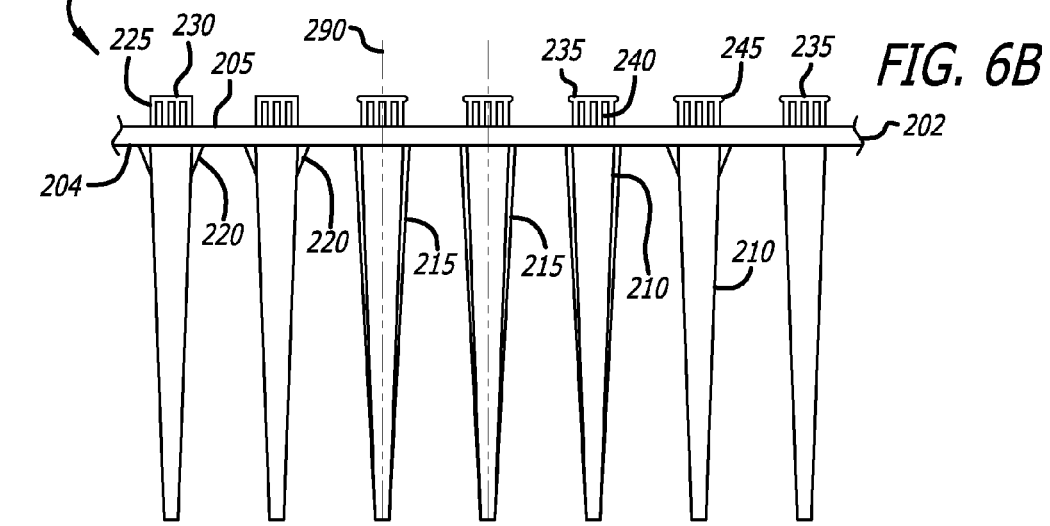
Figure 6C:
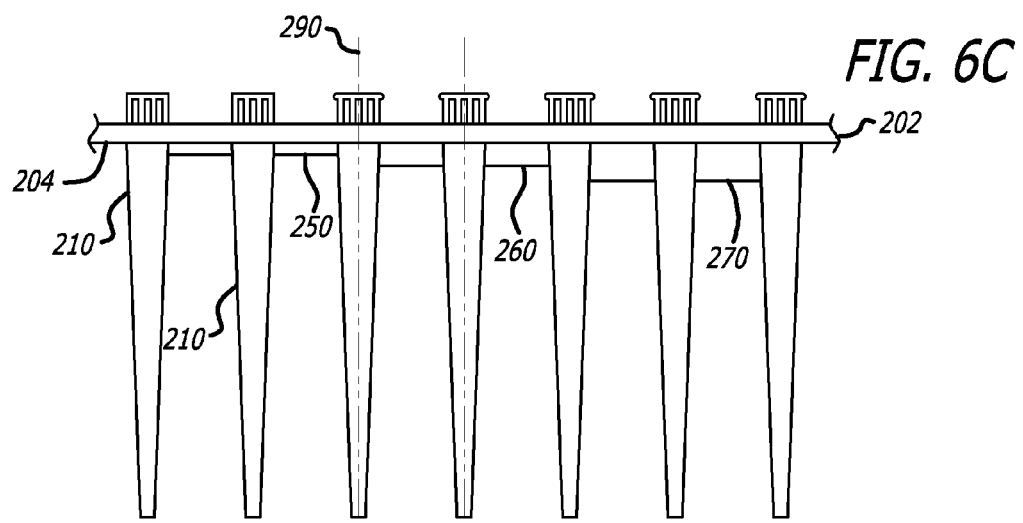

FIG. 6A shows embodiments in which a device comprises a plurality of sealing members 141 and/or 142, which sealing members can include sealing member ribs and/or depressions. A sealing member sometimes includes a flange 135 and sometimes includes no flange. Sealing member ribs or depressions 140 sometimes extend to flange 135 when present and form a rib/depression-flange interface 145. In embodiments where a flange is not present, sealing member ribs or depressions 143 can terminate at a point 144 along the length of the sealing member, and sometimes can terminate at the top perimeter of the sealing zone. Shown also in FIG. 6A is second surface 130 of the card and an outer surface 125 of pipette tips. FIG. 6B shows embodiments in which a device comprises a plurality of sealing members 225 that include a flange 235 or no flange, include ribs and/or depressions 240, rib or depression termini 245, sealing member top perimeter 230, second surface 204, pipette tip outer surface 210. Also shown in FIG. 6B is an axis extending through the pipette tip proximal region (e.g., around the top perimeter of the sealing member or the first surface of the card) and distal region (e.g., pipette tip bottom), and oriented at the center of the aperture, sealing member and pipette tip diameters. FIG. 6B also shows pipette tip stabilizing rib embodiments 220 and 215, which connect to the pipette tip outer surface and to the second surface of the card. FIG. 6C shows pipette tip stabilizing rib embodiments 250, 260 and 270 in connection with two pipette tips and the second surface of the card.

In some embodiments, integrated pipette tip device 40, 80 may be used to handle fluids by: engaging a dispensing device; drawing a fluid into pipette tips; and emitting the fluid in the pipette tips from the pipette tips. The integrated pipette tip device may be ejected from the dispensing device after the fluid is emitted from the pipette tips, in certain embodiments. In some embodiments the pipette tips of an integrated pipette tip device optionally may be rinsed at the washing station of a biological workstation configured with a suitable washing platform.

One-Piece Integrated Pipette Tip Device with Reinforcing Ribs

Figure 3A:
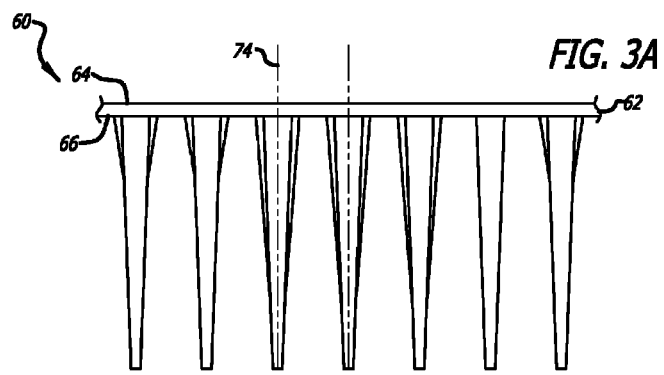
FIG. 3A illustrates a profile view of a one-piece device embodiment having reinforcing ribs.
Figure 5D:
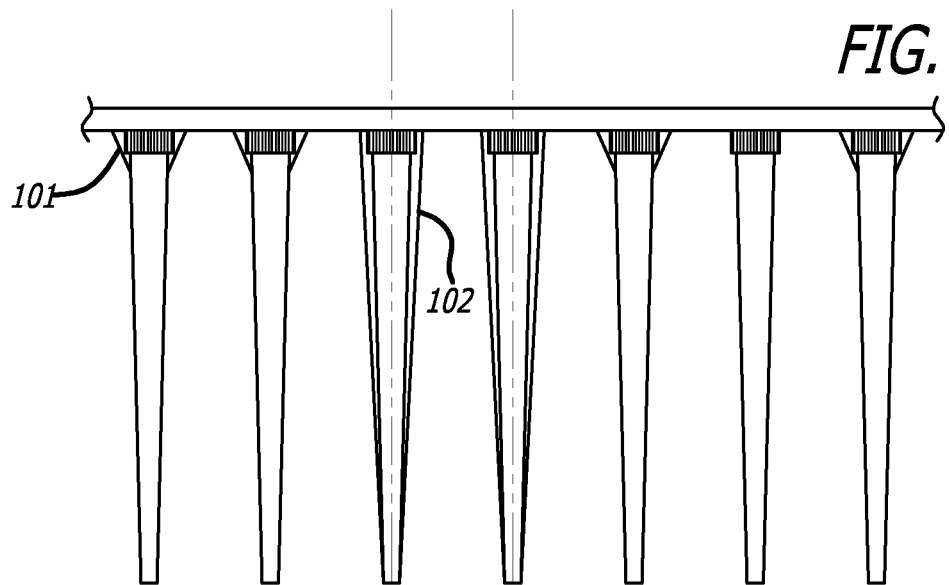
FIG. 5D illustrates a profile view of a device embodiment having proximal collars and various reinforcing rib embodiments. Reinforcing rib embodiments shown in FIG. 5A are substantially similar to rib embodiments illustrated in FIG. 3A.

In some embodiments, an integrated pipette tip device 60 may include a card 62 in connection with a plurality of pipette tips 68 and two or more ribs 70, 72 in connection with each pipette tip, as illustrated in FIG. 3A. Features described for cards 16, 42, and 80 can be incorporated into card 62 to generate one-piece integrated pipette tip devices with reinforcing ribs that include additional features found in other device embodiments described herein. Ribs 70 and 72 may co-extend from second surface 66, 81 and can extend from in the range of about one quarter 70 to about three quarters 72 of the length of distal portion of pipette tips 68, 86, in some embodiments. The length of the ribs can be of any dimension that does not interfere with subsequent liquid dispensing operations and provides adequate lateral support to maintain concentricity of upper and lower pipette tip openings. FIG. 5D shows rib embodiments 101 and 102 with cards having ribbed collar regions. Where ribs connect only to pipette tip surface 68 and bottom card surface 66 (e.g., rib 70), and do not attach to surfaces of two pipette tips (e.g., rib 74), each pipette tip often is in association with two or more such ribs. A card may include only one rib configuration (e.g., only rib 101 or rib 70 and not rib 102 or rib 72), and sometimes a card includes two or more rib configurations (e.g., ribs 70 and 72 in the same card).

Figure 3B:
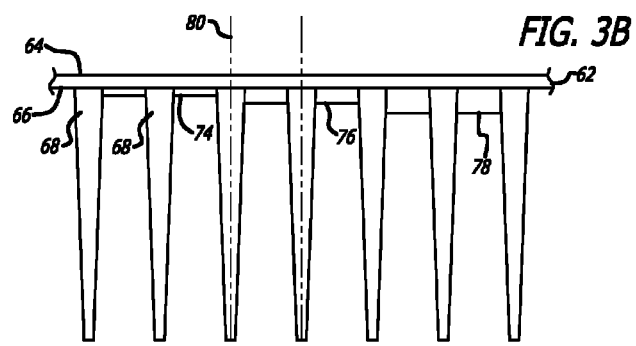
FIG. 3B illustrates a profile view of a one-piece device embodiment with reinforcing ribs interconnecting adjacent pipette tips.
Figure 3C:
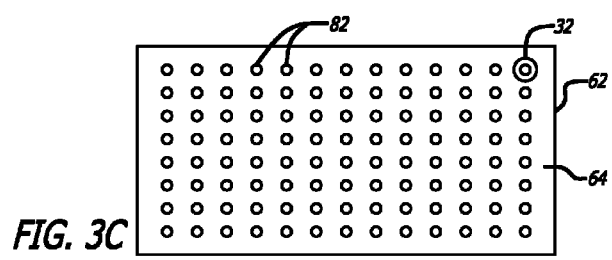
FIG. 3C shows a top view of the one-piece devices illustrated in FIGS. 3A and 3B.
Figure 5E:
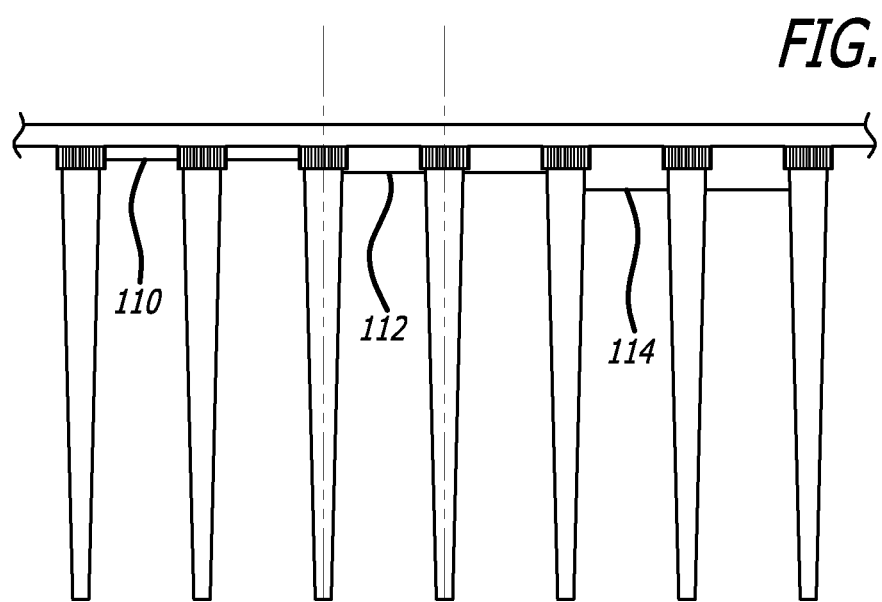
FIG. 5E illustrates a profile view of a device with proximal collars and reinforcing ribs interconnecting adjacent pipette tips. Reinforcing rib embodiments shown in FIG. 5E are substantially similar to rib embodiments illustrated in FIG. 3B.

In some embodiments, an alternative configuration of reinforcing ribs may be used, as illustrated in FIGS. 3B and 5E. Ribs 74, 76, and 78 interconnect two adjacent pipette tips 68, 86. Each pipette tip 68, 86 is still in connection with two or more ribs, although each rib connects two pipette tips, instead of two ribs being connected to one pipette tip, as illustrated in FIG. 3A. Ribs 74, 76 and 78 may be co-extruded from second surface 66, 81, and can extend from in the range of about one quarter 74 to about three quarters 78 of the length of distal portion of pipette tips 68, 86. Rib 76, as illustrated in FIG. 3B, is approximately one half the length of pipette tip 68. In some embodiments, a combination of ribs illustrated in FIGS. 3A, 5D, 3B and 5E may be used. Integrated pipette tip device 60, 80 may be configured to have ribs (70, 72, in FIG. 3A and the equivalent ribs illustrated in FIG. 5D) along the length of each pipette tip 68, 86 and also have horizontally interconnected ribs (74, 76 and 78, in FIG. 3B) between adjacent pipette tips. In some embodiments the two or more ribs in connection with each pipette tip can be in contact with an adjacent pipette tip distal region. FIG. 5E shows rib embodiments 110, 112 and 114 with cards having ribbed collar regions.

Where ribs attach to surfaces of two pipette tips (e.g., rib 74), each pipette tip often is in association with two or more such ribs. A card may include only one rib configuration (e.g., only rib 101 or rib 70 and not rib 102 or rib 72), and sometimes a card includes two or more rib configurations (e.g., ribs 70 and 72 in the same card). In certain embodiments, a card includes only ribs of type 70 and/or 72, and not type 74, 76 and/or 78, a card includes only ribs of type 74, 76 and/or 78 and not ribs of type 70 and/or 72, or a card includes ribs of type 74, 76 and/or 78 and ribs of type 70 and/or 72.

Card 62 also has a first surface 64 and an opposing second surface 66. As described above, the first and second surfaces are often substantially planar in shape, and substantially parallel to each other. In some embodiments, first (or upper) surface 64 may be substantially flat. One-piece integrated pipette tip device 60 also has symmetrical apertures 82 (illustrated in FIG. 3C) traversing the thickness of card 62 and a plurality of pipette tip 68 distal regions can extend from the second surface 66 of the card (illustrated in FIGS. 3A and 3B). In some embodiments, apertures 82 in card 62 are coaxially aligned and concentric with distal regions of each pipette tip 68. One-piece integrated pipette tip device 60 can also be referred to as a "one-piece ribbed device." One-piece ribbed devices sometimes optionally include substantially vertical sealing members that extend from the second surface of card 62 and the distal region of each pipette tip 68 extends from the sealing members. In embodiments including sealing members, the sealing members sometimes are ribbed sealing members and sometimes are non-ribbed sealing members. In certain embodiments, reinforcing ribs may be used to interconnect two adjacent pipette tips. The ribs can provide additional rigidity to decrease lateral displacement, or deviations in concentricity (e.g., bending or curving of thin walled pipette tips) that can sometimes occur with smaller pipette tips designed for dispensing devices having 96 or more nozzles. In some embodiments, annular protrusion 32 may be optionally included on the upper surface of integrated card 62, around apertures 82, which can aid sealing engagement of dispenser channels, and decrease the incidence of sample cross contamination, in some embodiments. In some embodiments annular protrusion 32 is made of the same material as the rest of the card, and in certain embodiments annular protrusion 32 is made of a different material from the rest of the card. In some embodiments, annular protrusion 32 is made from a polymer, and in certain embodiments annular protrusion is made from a thermoplastic elastomer. Non-limiting examples of thermoplastic elastomers suitable for use in annular protrusions are described herein.

In some embodiments, integrated pipette tip device 60 may be used to handle fluids by: engaging a dispensing device; drawing a fluid into pipette tips; and emitting the fluid in the pipette tips from the pipette tips. The integrated pipette tip device may be ejected from the dispensing device after the fluid is emitted from the pipette tips, in certain embodiments. In some embodiments the pipette tips of an integrated pipette tip device optionally may be rinsed at the washing station of a biological workstation configured with a suitable washing platform.

Although multiple configurations are shown in certain figures herein, it is understood that one device my include only one type of member shown or may include a combination of members. For example, a device may include only one type of pipette tip stabilizing rib embodiment shown in FIG. 6B or FIG. 6C, or a combination of such embodiments. A device also may include only one type of sealing member (e.g., a sealing member having a flange or a sealing member not having a flange (shown in FIG. 6A)), or a combination of sealing member embodiments. In another example, a device may include only one type of configuration around an aperture, such as no depression, no protrusion, a depression, a protrusion, no sealing member, a sealing member, or may include a combination of such configurations (e.g., FIG. 4H).
Features Common to One-Piece and Two-Piece Devices The pipette tip portion of an integrated pipette tip device can be of any geometry useful for dispensing fluids in combination with a dispensing device. The pipette tip portion of an integrated pipette tip device can be of any volume useful for dispensing fluids in combination with a dispensing device. The pipette tip portions extending below the lower surface of the card can be configured in sizes that hold from 0 to 10 microliters, 0 to 20 microliters, 1 to 100 microliters, 1 to 200 microliters and from 1 to 1000 microliters, for example. The external appearance of pipette tips may differ, and certain pipette tips can have a continuous tapered wall forming a central channel or tube that is roughly circular in horizontal cross section, in some embodiments. A pipette tip can have any cross-sectional geometry that results in a tip that (i) provides suitable flow characteristics, and (ii) can be fitted to a dispenser (e.g., pipette), for example.

Pipette tips sometimes have a cylindrical region which extends from the second surface of a card that acts as a sealing member for an inserted dispensing tool or apparatus. A sealing member sometimes is in contact with the first or second surface of a card, and sometimes another portion of a pipette tip, such as a portion of a distal region for example, is in contact with the first or second surface of a card. A terminal portion of a sealing member can be located about 0.126 inches to about 2.00 inches from the first or second surface of a card. A sealing member sometimes has a thickness of about 0.005 inches to about 0.015 inches. A top surface of a card can intersect each pipette tip in a pipette tip array at a cross sectional plane of the pipette tip, where the cross sectional plane is located at a point on a longitudinal axis intersecting the distal terminus and proximal terminus of the pipette tip. The point on the longitudinal axis sometimes is a distance from the distal terminus of the pipette tip equal to, or about equal to, 30% to 95% of the total length of the pipette tip from the distal terminus to the proximal terminus (e.g., a distance of about 35%, 40%, 45%, 50%, 55%, 60%, 65%, 70%, 75%, 80%, 85%, 90% the total length of the pipette tip). The distal portion or tapered portion of the pipette tip sometimes is co-extensive with the cylindrical sealing member which extends from the second surface of the pipette card. In some embodiments the sealing member is ribbed and in certain embodiments the sealing member is a non-ribbed proximal collar.

Pipette tips sometimes taper from the widest point at the top-most portion of the pipette tip (pipette proximal end or end that engages a dispenser), to a narrow opening at the bottom most portion of the pipette tip (pipette distal end that extends below the card or end used to acquire or dispel fluid). In certain embodiments, a pipette tip wall includes two or more taper angles. The inner surface of the pipette tip sometimes forms a tapered continuous wall, in some embodiments, and in certain embodiments, the external wall may assume an appearance ranging from a continuous taper to a stepped taper or a combination of smooth taper with external protrusions. The bore of the top-most portion of the central channel or tube generally is wide enough to accept a particular dispenser apparatus (e.g., nozzle, barrel).

The wall of the distal region of a pipette tip of Integrated pipette tip devices (e.g., the portion extending below the card or snap plate), sometimes is continuously tapered from the wider portion, which is in effective connection with the proximal section, to a narrower terminus. The wall of the distal region, in some embodiments, forms a stepped tapered surface. The angle of each taper in a distal region is between about zero degrees to about thirty degrees from the central longitudinal vertical axis of the pipette tip (e.g., about 0, 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 degrees), in certain embodiments. In some embodiments, the wall of the distal region forms stepped vertical sections. The wall thickness of a distal region may be constant along the length of the section, or may vary with the length of the section (e.g., the wall of the distal region closer to the proximal section of the pipette tip may be thicker or thinner than the wall closer to the distal region terminus; the thickness may continuously thicken of thin over the length of the wall). The distal region of a pipette tip generally terminates in an aperture through which fluid passes into or out of the distal portion. A distal region of a pipette tip may contain a filter, insert or other material.

The wall of the proximal section of devices described herein (e.g., portion contained within the thickness of the card, or projecting above the upper surface of the card or projecting below the lower surface of the card) sometimes is continuously tapered from the top portion, to a narrower terminus, sometimes is stepped from a region of constant circumference to a continuously tapered region from an upper portion to a narrower terminus, and sometimes is not tapered and/or not stepped. In some embodiments the region of constant circumference is a ribbed sealing member. In certain embodiments, the contribution of the constant circumference portion to the total length of the pipette tip extending below the second surface of the card is about ⅓ of the total length of the pipette tip.

The top portion generally is open and often is shaped to receive a pipette tip engagement portion of a dispensing device. The wall of a proximal section, in some embodiments, forms a stepped tapered surface. The angle of each taper in the proximal section is between about zero degrees to about thirty degrees from the central longitudinal vertical axis of the pipette tip (e.g., about 0,1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 degrees), in certain embodiments. The wall thickness of a proximal section may be constant over the length of the section, or may vary with the length of the proximal section (e.g., the wall of the proximal section closer to the distal region of the pipette tip may be thicker or thinner than the wall closer to the top of the proximal section; the thickness may continuously thicken or thin over the length of the wall). A proximal section of a pipette tip may contain a filter, insert or other material.

The interior bore of a pipette tip, in the distal region or proximal region, or distal region and proximal region, sometimes is substantially cylindrical and often is substantially frustrum shaped (e.g., bore 19a or 19a' in FIGS. 1E and 1F, and bore 53 in FIGS. 2C, 2D, 2F, 4A, 4B, 4C, 4D, 4E, 4F and 4G).

Integrated pipette tip devices described herein often are configured for use with standard pipette tip storage units. The cards can be configured to have substantially the same planar shape and dimensions as commercially available pipette tip storage boxes or storage units. A card often is substantially rectangular in shape, where the length of one set of parallel sides can be in the range of about 120 to about 140 millimeters, and more specifically between about 125 to about 135 millimeters, in some embodiments (e.g., about 120 millimeters, about 125 millimeters, about 126 millimeters, about 127 millimeters, about 128 millimeters, about 129 millimeters, about 130 millimeters, about 131 millimeters, about 132 millimeters, about 133 millimeters, about 134 millimeters, about 135 millimeters, or about 140 millimeters). The second set of parallel sides can be in the range of about 70 to about 100, and more specifically about 80 to about 90 millimeters, in some embodiments (e.g., about 70 millimeters, about 75 millimeters, 80 millimeters, about 81 millimeters, about 82 millimeters, about 83 millimeters, about 84 millimeters, about 85 millimeters, about 86 millimeters, about 87 millimeters, about 88 millimeters, about 89 millimeters, about 90 millimeters, about 95 millimeters, or about 100 millimeters). The integrated cards can range in thickness from about 0.5 to about 5 milliliters, in certain embodiments (e.g., about 0.5 millimeters, about 0.6 millimeters, about 0.7 millimeters, about 0.8 millimeters, about 0.9 millimeters, about 1.0 millimeter, about 1.1 millimeters, about 1.2 millimeters, about 1.3 millimeters, about 1.4 millimeters, about 1.5 millimeters, about 1.6 millimeters, about 1.7 millimeters, about 1.8 millimeters, about 1.9 millimeters, about 2.0 millimeters, about 2.1 millimeters, about 2.2 millimeters, about 2.3 millimeters, about 2.4 millimeters, about 2.5 millimeters, about 2.6 millimeters, about 2.7 millimeters, about 2.8 millimeters, about 2.9 millimeters, about 3.0 millimeters, about 3.1 millimeters, about 3.2 millimeters, about 3.3 millimeters, about 3.4 millimeters, about 3.5 millimeters, about 3.6 millimeters, about 3.7 millimeters, about 3.8 millimeters, about 3.9 millimeters, about 4.0 millimeters, about 4.1 millimeters, about 4.2 millimeters, about 4.3 millimeters, about 4.4 millimeters, about 4.5 millimeters, about 4.6 millimeters, about 4.7 millimeters, about 4.8 millimeters, about 4.9 millimeters, or about 5.0 millimeters). The thickness of the cards is from about 20% to about 80% of the overall height of the card.

Pipette tips of the one-piece and two-piece integrated cards often are arranged in substantially planar arrays. The term "array" as used herein refers to an arrangement of pipette tips across a two-dimensional surface. An array may be of any convenient general shape (e.g., circular, oval, square, rectangular). An array may be referred to as an "X by Y array" for square or rectangular arrays, where the array includes X number of pipette tips in one dimension and Y number of pipette tips in a perpendicular dimension. For example, a "12 by 8 array" includes twelve pipette tips in one dimension and eight pipette tips in a perpendicular dimension, where the array includes a total of ninety-six (96) pipette tips. An array may be symmetrical (e.g., a 16 by 16 array) or non-symmetrical (e.g., an 8 by 16 array). An array may include any convenient number of pipette tips in any suitable arrangement. For example, X or Y independently can be 1 to 64 (e.g., 2, 3, 4, 5, 6, 7, 8, 9, 10, 11, 12, 13, 14, 15, 16, 17, 18, 19, 20, 22, 24, 26, 28, 30, 32, 34, 36, 38, 40, 42, 44, 46, 48, 50, 52, 54, 56, 58, 60, 62), and sometimes independently can be 6, 12, 16, 24, 32, 48 or 64. In some embodiments, X multiplied by Y yields 96, 384 or 1536, and sometimes arrays provided in a tray total to 96, 384 or 1536 pipette tips. Non-limiting examples of array configurations with 96, 384 or 1536 pipette tips are: a 12 by 8 or 6 by 16 array for configurations of 96 tips, a 24 by 16, 12 by 32 or 8 by 48 array for configurations of 384 tips, and a 24 by 64 or 48 by 32 array for configurations of 1536 tips. In some embodiments, the one and two-piece integrated pipette tip devices (20, 40, and 60) include 384 pipette tips. In some embodiments, the one and two-piece integrated pipette tip devices (20, 40, and 60) include 1536 pipette tips.

In some embodiments, one and two-piece integrated pipette tip devices (20, 40, and 60) can be configured as sub-regions in a rack, or multiple regions may be provided in a rack. For example, a rack may contain two or more integrated pipette tip devices or regions, in some embodiments (e.g., 2, 3, 4, 5, 6, 7, 8, 9, 10, 11, 12, 13, 14, 15, 16, 17, 18, 19, 20, 21, 22, 23 or 24 separate devices or regions in one rack). In certain embodiments, an edge of each separate device or region is connected to an edge of another separate region. In certain embodiments, an integrated pipette tip device may be separated into two or more sub-regions (e.g., 2, 3, 4, 5, 6, 7, 8, 9, 10, 11, 12, 13, 14, 15, 16, 17, 18, 19, 20, 21, 22, 23 or 24 sub-regions in one rack). A sub-region in some embodiments is a quadrant. A card including 384 or 1536 pipette tips, can be divided into four sub-regions, each containing 96, or 384 pipette tips, respectively. The demarcation between the sub-regions can be an area of scoring or a frangible area to allow the card to be used in a modular fashion. Individual sub-regions may be separated (e.g., completely separate, induced separation) to allow a subset of the pipette tips to be used, as desired by the operator. In some embodiments, for a rack providing an integrated pipette tip device having sub-regions that can be separated, the attractive force (e.g., frictional force) between the pipette tips and nozzles of a dispenser for one sub-region is greater than the attractive force between sub-regions, which allows the dispensing device to pull each sub-region from the rack independent of other sub-regions. In certain embodiments, for a rack providing multiple integrated pipette tip devices, the attractive force between the pipette tips and nozzles of a dispenser for each region is greater than the attractive force between regions, which allows the dispensing device to pull each region from the rack independent of other regions.

In some embodiments, the card portion of one and two-piece integrated pipette tip devices (20, 40, 60 and 80) can be constructed from a first material and the gasket in two-piece devices may be constructed from a second material relatively more resilient than the first material. In some embodiments the first material may be a moldable plastic. In some embodiments, the annular protrusion protruding above the first surface of one and two-piece integrated pipette tip devices is made from the same material as the card, and in certain embodiments, the annular protrusion protruding above the first surface of one or two-piece integrated pipette tip devices may be constructed from a second material relatively more resilient than the first material (e.g., the material of the card). Non-limiting examples of moldable plastics include, polypropylene (PP), polyethylene (PE), high-density polyethylene, low-density polyethylene, polyethylene teraphthalate (PET), polyvinyl chloride (PVC), polytetrafluoroethylene (PTFE), polystyrene (PS), high-density polystyrene, acrylnitrile butadiene styrene copolymers, plastics with higher flow and lower viscosity or a combination of two or more of the foregoing.

Non-limiting examples of plastics with higher flow and lower viscosity include, any suitable material having a hardness characterized by one or more of the following properties, in certain embodiments: a melt flow rate (230 degrees Celsius at 2.16 kg) of about 30 to about 75 grams per 10 minutes using an ASTM D 1238 test method; a tensile strength at yield of about 3900 to about 5000 pounds per square inch using an ASTM D 638 test method; a tensile elongation at yield of about 7 to about 14% using an ASTM D 638 test method; a flexural modulus at 1% sectant of about 110,000 to about 240,000 pounds per square inch using an ASTM D 790 test method; a notched Izod impact strength (23 degrees Celsius) of about 0.4 to about 4.0 foot pounds per inch using an ASTM D 256 test method; and/or a heat deflection temperature (at 0.455 MPa) of about 150 degrees to about 500 degrees Fahrenheit using an ASTM D 648 test method. A material used to construct the pipette tips and card include moldable materials in some embodiments. Non-limiting examples of materials that can be used to manufacture the pipette tips and cards include polypropylene, polystyrene, polyethylene, polycarbonate, and the like, and mixtures thereof.

Materials suitable for use in embodiments described herein, and methods for manufacture using those materials have been described in published United States Patent Application No. 20100218622, filed on Jan. 11, 2010, and entitled "FLEXIBLE PIPETTE TIPS", the entirety of which is hereby incorporated by reference herein.

In some embodiments a substantially resilient material comprising a moldable thermoplastic elastomer (TPE) is used to manufacture the gasket portion of a two-piece integrated pipette tip device and/or a sealing member. Non-limiting examples of TPE's include, styrenic block copolymers, polyolefin blends, elastomeric alloys, thermoplastic polyurethanes, thermoplastic copolyester and thermoplastic polyamides. Examples of TPE products from the block copolymers group are STYROFLEX (BASF), KRATON (Shell Chemicals), PELLETHANE (Dow chemical), PEBAX, ARNITEL (DSM), HYTREL (Du Pont) and more. Examples of commercially available elastomeric alloys include SANTOPRENE (in-situ cross linked polypropylene and EPDM rubber; Monsanto), GEOLAST (Monsanto) and ALCRYN (Du Pont). Further examples of the materials that can be used to construct the annular protrusion include, without limitation, thermoplastic vulcanizates (TPV; SANTOPRENE TPV), thermoplastic polyurethane (TPU), thermoplastic olefins (TPO), polysulfide rubber, ethylene propylene rubber (e.g., EPM, a copolymer of ethylene and propylene), ethylene propylene diene rubber (e.g., EPDM, a terpolymer of ethylene, propylene and a diene-component), epichlorohydrin rubber (ECO), polyacrylic rubber (ACM, ABR), silicone rubber (SI, Q, VMQ), fluorosilicone Rubber (FVMQ), fluoroelastomers (e.g., FKM, and FEPM, VITON, TECNOFLON, FLUOREL, AFLAS and DAI-EL), perfluoroelastomers (e.g., FFKM, TECNOFLON PFR, KALREZ, CHEMRAZ, PERLAST), polyether block amides (PEBA), chlorosulfonated polyethylene (CSM, e.g., HYPALON), ethylene-vinyl acetate (EVA), synthetic polyisoprene (IR), butyl rubber (copolymer of isobutylene and isoprene, IIR), halogenated butyl rubbers (chloro butyl rubber: CIIR; bromo butyl rubber: BIIR), polybutadiene (BR), styrene-butadiene rubber (copolymer of polystyrene and polybutadiene, SBR), nitrile rubber (copolymer of polybutadiene and acrylonitrile, NBR; Buna N rubbers), hydrogenated nitrile rubbers (HNBR, THERBAN and ZETPOL), chloroprene rubber (CR, polychloroprene, NEOPRENE, BAYPREN) and the like.

Substantially resilient sealing members (e.g., including an elastomeric material (e.g., TPE)) can be associated with a device by any suitable method. In some embodiments, a sealing member is manufactured as a separate element and is pressed onto a device. Such a separate element can be affixed to the device by friction and optionally is affixed to the device by a suitable adhesive. In certain embodiments, a sealing member is molded onto a device. A sealing member can be molded onto a device as part of a double-shot molding process, where the card and pipette tips are molded in one shot and the sealing members are molded in another shot, for example.

In some embodiments anti-microbial agents or substances may be added to the moldable plastic during the manufacture process. In some embodiments, the anti-microbial agent or substance can be an anti-microbial metal. The addition of anti-microbial agents may be useful in (i) decreasing the amount of microbes present in or on a device, (ii) decreasing the probability that microbes reside in or on a device, and/or (iii) decreasing the probability that microbes form a biofilm in or on a device, for example. Non-limiting examples of metals with anti-microbial properties are silver, gold, platinum, palladium, copper, iridium (i.e. the noble metals), tin, antimony, bismuth, zinc cadmium, chromium, and thallium. The aforementioned metal ions are believed to exert their effects by disrupting respiration and electron transport systems upon absorption into bacterial or fungal cells. A commercially accessible form of silver that can be utilized in devices described herein is SMARTSILVER NovaResin. SMARTSILVER NovaResin is a brand of antimicrobial master batch additives designed for use in a wide range of polymer application. Billions of silver nanoparticles can easily be impregnated into PET, PP, PE and nylon using standard extrusion or injection molding equipment. SMARTSILVER NovaResin additives may be delivered as concentrated silver-containing master batch pellets to facilitate handling and processing. NovaResin is designed to provide optimum productivity in a wide range of processes, including fiber extrusion, injection molding, film extrusion and foaming.

Further non-limiting examples of anti-microbial substances or agents include, without limitation, inorganic particles such as barium sulfate, calcium sulfate, strontium sulfate, titanium oxide, aluminum oxide, silicon oxide, zeolites, mica, talcum, and kaolin. Methods of manufacture of anti-microbial containing plastics, and amounts of anti-microbial substances used in manufacture of anti-microbial containing plastics have been described in published United States Patent Application No. 20110259443, filed on Dec. 16, 2010, and entitled "ANTIMICIROBIAL FLUID HANDLING DEVICES AND METHODS OF MANUFACTURE", the entirety of which is hereby incorporated herein by reference.

In certain embodiments anti-static agents can be incorporated into the moldable plastic during the manufacture process. In certain embodiments, an anti-static agent can be an electrically conductive member. In certain embodiments, an integrated pipette tip device is in contact with an electrically conductive member, or portions thereof, which is in communication with the interior or exterior of a pipette tip storage unit. This contact may allow the static charge from the pipette tips to be discharged.

An electrically conducting member may include any type of electrically conductive material, such as a conductive metal for example. Non-limiting examples of electrically conductive metals include, platinum (Pt), palladium (Pd), copper (Cu), nickel (Ni), silver (Ag) and gold (Au). The metals may be in any form in or on the conductive member, for example, such as metal flakes, metal powder, metal strands or coating of metal. An electrically conductive member, or portions thereof, may include a metal, polymeric material, foam, film, sheet, foil, salt or combinations thereof. In some embodiments, a conductive metal foil may be utilized for one or more components of a pipette tip tray (e.g., copper-aluminum foil; label adhered to an electrically conductive tab on exterior of a pipette tip tray component).

The electrically conductive materials, or portions thereof, may be any material that can contain movable electric charges, for example such as carbon. In some embodiments, the electrically conductive member includes about 5% to about 40% or more carbon by weight (e.g., 7-10%, 9-12%, 11-14%, 13-16%, 15-18%, 17-20%, 19-22%, 21-24%, 23-26%, 25-28%, 27-30%, 29-32%, 32-34%, 33-36%, or 35-38% carbon by weight). In certain embodiments, an electrically conductive film is utilized that includes carbon (e.g., commercially available from Gemini Plastic Enterprises, Inc., California). An electrically conductive film in some embodiments contains ethylene vinyl acetate (EVA), which can impart a supple quality to the film (e.g., about 5% to about 25% EVA by weight; about 6, 7, 8, 9, 10, 11, 12, 13, 14, 15, 16, 17, 18, 19, 20, 21, 22, 23, 24% EVA). Methods of manufacture of anti-static member containing plastics, and amounts of anti-static members used in manufacture of anti-static member containing plastics have been described in published United States Patent Application No. 20100221151, filed on Jan. 22, 2010, and entitled "ANTI-STATIC PIPETTE TITRAYS", and is hereby incorporated herein, in its entirety.

In some embodiments, the proximal region, or a portion thereof, of pipette tips in an integrated pipette tip device does not project beyond the upper surface of the card with which the pipette tips are integrated (e.g., aperture openings of the pipette tips are co-extensive with the upper surface of the card in one-piece devices). In certain embodiments, apertures of each pipette tip member in an integrated pipette tip device are surrounded by material that is about 2 millimeters thick or less (e.g., in a one-piece device). In particular embodiments, the thickness of pipette tip elements and/or the card element in a device is greater than about 0.1 millimeter. In certain embodiments, a device does not include, and is not used in conjunction with, a flexible component (e.g., planar component) that covers, and/or seals, an opening of a pipette tip proximal region.

In some embodiments, integrated pipette tip devices that are used to present 96, 384 or 1536 pipette tips in a rack can deliver a volume of double distilled water with a CV of 10% or less, when the pipettor is set at a low or minimum volume. In certain embodiments, integrated pipette tip devices that are used to present 96, 384 or 1536 pipette tips in a rack can deliver volume of double distilled water with a CV of 5% or less, when the pipettor is set at a high or maximum volume. The precision and accuracy measurements of the pipette tips is dependent on the condition and calibration of the pipettor being tested with the tips described herein. In general, accuracy and CV values for devices described herein can range between 1% and 10% depending on the volume at which the pipettor is tested, and the condition and calibration of the pipettor.

Pipette tip "precision" refers to the ability of a plurality of pipette tips to deliver about the same volume of fluid, with a relatively small standard deviation, for a given dispenser (e.g., pipette tips stated to deliver 200 microliters of fluid consistently deliver about 197 microliters of fluid). Pipette tip "accuracy" refers to the ability of a plurality of pipette tips to deliver a particular volume of fluid (e.g., pipette tips stated to deliver 200 microliters of fluid deliver, in practice, about 200 microliters of fluid). One measure of pipette tip precision is a calculated percent "coefficient of variation," which also is referred to herein as "CV" and discussed in greater detail hereafter.

Coefficient of variation (CV) can be calculated for a pipette tip lot in a variety of manners. In general, percent CV equals (a) the quotient of (i) standard deviation in volume dispensed from the pipette tips, divided by (ii) the average volume dispensed from the pipette tips, (b) multiplied by 100. A CV value often is calculated for a particular lot of pipette tips. One of many protocols can be selected for collecting pipette tips in the lot to calculate a CV value. Random pipette tips may be selected from a lot after a manufacturing run is completed in some embodiments, and in certain embodiments, pipette tips are collected at different time points during the manufacturing run of the lot (e.g., pipette tips are collected at time points during the manufacture run at regular intervals).

In certain embodiments pertaining to CV measurements, water is dispensed from pipette tips of a particular lot using one dispensing device, and volume of each dispensed amount is weighed. The average and standard deviation of all weighed aliquots of water then can be calculated in such embodiments.

In some embodiments pertaining to CV measurements, liquid containing a dye is dispensed from each pipette tip into a well of a tray having an array of wells. The average volume can be determined from the weight of the plate containing the dispensed liquid less the weight of the plate before liquid was dispensed. The standard deviation in volume dispensed into each well can be determined by optically determining the volume in each well by the amount of dye in each well (e.g., using a light, fluorescence, luminescence or absorbance detector in a plate reader).

EXAMPLES

The example set forth below illustrates, and does not limit, the technology.

Example 1

Examples of Embodiments

Described hereafter are non-limiting examples of certain embodiments.

A1. A two-piece integrated pipette tip device, including a card in connection with a plurality of integrated pipette tips and a gasket in sealing connection with a first surface of the card, which card and pipette tips are constructed from a first material and the gasket is constructed from a second material relatively more resilient than the first material;

each of which pipette tips includes a distal region and each pipette tip extends from a second surface of the card opposite the first surface;

which gasket includes a surface in connection with the first surface of the card, which surface of the gasket covers about 80% or more of the first surface of the card;

which card includes card apertures defining channels that traverse the thickness of the card, each of which card apertures is concentric with one pipette tip; and which gasket includes gasket apertures that traverse the thickness of the card, each of which gasket apertures is concentric with one card aperture.

A2. The device of embodiment A1, wherein the gasket includes annular gasket protrusions surrounding the gasket apertures.

A3. The device of embodiment A2, wherein each gasket protrusions is configured to sealingly engage an inner surface of one card aperture.

A4. The device of embodiment A2, wherein the card includes annular card depressions surrounding the card apertures, which card depressions are concentric with the card apertures and each of which card depressions is configured to sealingly engage with one gasket protrusion.

A5. The device of embodiment A1, wherein the card includes annular card protrusions extending from the first surface, which card protrusions surround the card apertures and are concentric with the card apertures.

A6. The device of embodiment A5, wherein each of the card protrusions is configured to sealingly engage with an inner surface of one gasket aperture.

A7. The device of embodiment A5, wherein the gasket includes annular gasket depressions surrounding the gasket apertures, which gasket depressions are concentric with the gasket apertures and each of which gasket depressions is configured to sealingly engage with one card protrusion.

A8. The device of any one of embodiments A1 to A7, wherein the surface of the gasket in connection with the first surface of the card covers about 90% or more of the first surface of the card.

A9. The device of embodiment A6, wherein the surface of the gasket in connection with the first surface of the card covers about 95% or more of the first surface of the card.

A10. The device of embodiment A9, wherein the surface of the gasket in connection with the first surface of the card covers about 100% or more of the first surface of the card.

A11. The device of any one of embodiments A1 to A10, wherein the first material is a moldable plastic.

A12. The device of embodiment A11, wherein the plastic includes one or more of polypropylene (PP), polyethylene (PE), high-density polyethylene, low-density polyethylene, polyethylene teraphthalate (PET), polyvinyl chloride (PVC), polyethylenefluoroethylene (PEFE), polystyrene (PS), high-density polystyrene, acryInitrile butadiene styrene copolymers, or a combination of two or more of the foregoing.

A13. The device of embodiment A12, wherein the plastic includes PE.

A14. The device of any one of embodiments A1 to A13, wherein the second material includes a moldable thermoplastic elastomer.

A15. The device of any one of embodiments A1 to A14, wherein the device includes 384 pipette tips.

A16. The device of any one of embodiments A1 to A14, wherein the device includes 1536 pipette tips.

A17. The device of any one of embodiments A1 to A16, wherein the gasket is substantially flat.

A18. The device of any one of embodiments A1 to A17, wherein the distal region is in connection with the second surface of the card.

A19. The device of any one of embodiments A1 to A18, further including a plurality of pipette tip support ribs, each of which pipette tip support ribs is in connection with a pipette tip and the second surface of the card.

A20. The device of embodiment A19, wherein each pipette tip support rib is in contact with the distal region of a pipette tip.

A21. The device of embodiment A19 or A20, wherein each pipette tip support rib is in contact with two pipette tips.

A22. The device of embodiment A19 or A20, wherein each pipette tip support rib is in contact with one pipette tip and no other pipette tip.

B1. A method for dispensing a fluid by an integrated pipette tip device, including:
engaging a dispensing device with a device of any one of embodiments A1 to A22,
drawing a fluid into the pipette tips of the integrated pipette tip device, and dispensing the fluid from the pipette tips.

B2. The method of embodiment B1, which includes ejecting the integrated pipette tip device after the fluid is ejected from the pipette tips.

C1. An integrated pipette tip device, including:
a substantially flat card including a first surface and an opposing second surface, which card includes a plurality of apertures, each aperture defining the opening of a channel traversing the thickness of the card;
which card includes a plurality of integrated pipette tips, each of which pipette tips including a distal region that effectively extends from the second surface of the card and is concentric with one aperture; and
which card includes a plurality of bores, each of which bores having an opening on the first surface of the card located at the intersection of four adjacent apertures, and which bores extend through at least a portion of the thickness of the card.

C2. The device of embodiment C1, wherein the thickness of the card between the first surface and the second surface is about 0.5 to about 5 millimeters.

C3. The device of embodiment C1 or C2, wherein the first surface of the card includes one or more depressions, each of with depressions surrounds one aperture of the card, and each of which depressions is concentric with the aperture.

C4. The device of any one of embodiments C1 to C3, wherein the first surface of the card includes one or more protrusions, each of with protrusions surrounds one aperture of the card, and each of which protrusions is concentric with the aperture.

C5. The device of embodiment C4, wherein the protrusion includes a protrusion surface parallel to the first surface of the card, which protrusion surrounds a depression depressed from the protrusion surface, which depression surrounds one of the apertures of the card, and which protrusion is concentric with the depression and the aperture.

C6. The device of any one of embodiments C3 to C5, which includes a plurality of depressions or a plurality of protrusions, or a plurality of depressions and a plurality of protrusions.

C7. The device of embodiment C6, wherein each aperture of the card is effectively surrounded by one depression or one protrusion, or one depression and one protrusion.

C8. The device of any one of embodiments C3 to C7, wherein the protrusions are annular protrusions.

C9. The device of any one of embodiments C3 to C8, wherein the depressions are annular depressions.

C10. The device of any one of embodiments C1 to C9, wherein the distal regions of the pipette tips are in connection with the second surface.

C11. The device of any one of embodiments C1 to 010, further including a plurality of dispenser sealing members, each of which dispenser sealing members including an opening in effective association with one channel of the card.

C12. The device of embodiment C11, wherein the sealing member extends from the second surface of the card and the distal region of each pipette tip extends from the sealing member.

C13. The device of embodiment C11, wherein the sealing member is connected to the first surface of the card.

C14. The device of embodiment C11, wherein the sealing member is connected to or is seated in a protrusion surface.

C15. The device of embodiment C11, wherein the sealing member is connected to or is seated in a depression.

C16. The device of any one of embodiments C13 to C15, wherein each sealing member includes a flange surrounding the outer perimeter of the sealing member.

C17. The device of any one of embodiments C11 to C16, wherein the exterior surface of the sealing member includes no sealing member ribs, no sealing member depressions, sealing member ribs, sealing member depressions or a combination thereof.

C18. The device of embodiment C17, wherein the sealing member includes no sealing member ribs and no sealing member depressions.

C19. The device of embodiment C17, wherein the sealing member ribs or sealing member depressions are parallel to an axis extending from the aperture of the card to the distal region of the pipette tip.

C20. The device of embodiment C17 or C19, wherein the sealing member ribs include first ribs and second ribs, which first ribs and second ribs alternate along the circumference of the exterior surface of the sealing member, which first ribs are of a first thickness and which second ribs are of a second thickness, and which first thickness is different than the second thickness.

C21. The device of any one of embodiments C17, C19 and C20, wherein the sealing member includes sealing member ribs, sealing member depressions or a combination thereof, and wherein one or more of the ribs or depressions contact the flange.

C22. The device of any one of embodiments C11 to C21, wherein the sealing member is an annular sealing member.

C23. The device of any one of embodiments C11 to C22, wherein the sealing member includes an exterior wall that is substantially vertical to the first surface of the card or the second surface of the card.

C24. The device of any one of embodiments C11 to C23, wherein the sealing member includes a flexible material not present in the card or in the pipette tips.

C25. The device of any one of embodiments C11 to C23, wherein the sealing member contains the same material as the card and the pipette tips.

C26. The device of any one of embodiments C1 to C25, further including a plurality of pipette tip support ribs, each of which pipette tip support ribs is in connection with a pipette tip and the second surface of the card.

C27. The device of embodiment C26, wherein each pipette tip support rib is in contact with the distal region of a pipette tip.

C28. The device of embodiment C26 or C27, wherein each pipette tip support rib is in contact with two pipette tips.

C29. The device of embodiment C26 or C27, wherein each pipette tip support rib is in contact with one pipette tip and no other pipette tip.

C30. The device of any one of embodiments C26 to C29, wherein the pipette tip support rib is in contact with a sealing member extending from the second surface of the card.

C31. The device of any one of embodiments C1 to C30, wherein the bores extend through the entire thickness of the card.

C32. The device of any one of embodiments C1 to C31, wherein the opening of each of the bores is substantially square shaped or diamond shaped.

C33. The device of embodiment C32, wherein each side of the square shaped or diamond shaped opening is a curved side.

C34. The device of embodiment C33, wherein each aperture of the card is circular and the radius of curvature of each curved side of each bore is greater than, and substantially follows, the radius of curvature of the circular aperture.

C35. The device of any one of embodiments C1 to C34, wherein the first surface is substantially flat and includes no protrusions and no sealing members.

C36. The device of embodiment C35, wherein the first surface includes no depressions.

C37. The device of embodiment C35, wherein the first surface includes depressions, each depression surrounding one aperture of the card.

D1. An integrated pipette tip device, including:
a substantially flat card including a first surface and an opposing second surface, which card includes a plurality of apertures, each aperture defining the opening of a channel traversing the thickness of the card;
which card includes a plurality of integrated pipette tips, each of which pipette tips including a distal region that effectively extends from the second surface of the card and is concentric with one aperture; and
which card includes a plurality of dispenser sealing members, each of which sealing members including an opening in effective association with one channel of the card, and each of which sealing members (i) is in connection with the second surface of the card and the distal region of a pipette tip, or (ii) is in effective connection with the first surface of the card and includes one or more sealing member ribs, one or more sealing member depressions, a flange, a flexible material not present in the card or pipette tips, or combination thereof.

D2. The device of embodiment D1, wherein the thickness of the card between the first surface and the second surface is about 0.5 to about 5 millimeters.

D3. The device of embodiment D1 or D2, wherein the first surface of the card includes one or more depressions, each of with depressions surrounds one aperture of the card, and each of which depressions is concentric with the aperture.

D4. The device of any one of embodiments D1 to D3, wherein the first surface of the card includes one or more protrusions, each of with protrusions surrounds one aperture of the card, and each of which protrusions is concentric with the aperture.

D5. The device of embodiment D4, wherein the protrusion includes a protrusion surface parallel to the first surface of the card, which protrusion surrounds a depression depressed from the protrusion surface, which depression surrounds one of the apertures of the card, and which protrusion is concentric with the depression and the aperture.

D6. The device of any one of embodiments D3 to D5, which includes a plurality of depressions or a plurality of protrusions, or a plurality of depressions and a plurality of protrusions.

D7. The device of embodiment D6, wherein each aperture of the card is effectively surrounded by one depression or one protrusion, or one depression and one protrusion.

D8. The device of any one of embodiments D3 to D7, wherein the protrusions are annular protrusions.

D9. The device of any one of embodiments D3 to D8, wherein the depressions are annular depressions.

D10. The device of any one of embodiments D1 to D9, wherein the distal regions of the pipette tips are in connection with the second surface.

D11. The device of any one of embodiments D1 to D10, wherein the sealing member is an annular sealing member.

D12. The device of any one of embodiments D1 to D11, wherein the sealing member extends from the second surface of the card and the distal region of each pipette tip extends from the sealing member.

D13. The device of any one of embodiments D1 to D11, wherein the sealing member is connected to the first surface of the card.

D14. The device of any one of embodiments D1 to D11, wherein the sealing member is connected to or is seated in a protrusion surface.

D15. The device of any one of embodiments D1 to D11, wherein the sealing member is connected to or is seated in a depression.

D16. The device of any one of embodiments D13 to D15, wherein each sealing member includes a flange surrounding the outer perimeter of the sealing member.

D17. The device of embodiment D12, wherein the exterior surface of the sealing member includes no sealing member ribs, no sealing member depressions, sealing member ribs, sealing member depressions or a combination thereof.

D18. The device of embodiment D17, wherein the sealing member includes no sealing member ribs and no sealing member depressions.

D19. The device of any one of embodiments D1 to D17, wherein the sealing member ribs or sealing member depressions are parallel to an axis extending from the aperture of the card to the distal region of the pipette tip.

D20. The device of any one of embodiments D1 to D17 and D19, wherein the sealing member ribs include first ribs and second ribs, which first ribs and second ribs alternate along the circumference of the exterior surface of the sealing member, which first ribs are of a first thickness and which second ribs are of a second thickness, and which first thickness is different than the second thickness.

D21. The device of any one of embodiments D1 to D17, D19 and D20, wherein the sealing member includes sealing member ribs, sealing member depressions or a combination thereof, and wherein one or more of the ribs or depressions contact the flange.

D22. The device of any one of embodiments D1 to D21, wherein the sealing member includes an exterior wall that is substantially vertical to the first surface of the card or the second surface of the card.

D23. The device of any one of embodiments D1 to D23, wherein the sealing member includes a flexible material not present in the card or in the pipette tips.

D24. The device of any one of embodiments D1 to D23, wherein the sealing member contains the same material as the card and the pipette tips.

D25. The device of any one of embodiments D1 to D24, further including a plurality of pipette tip support ribs, each of which pipette tip support ribs is in connection with a pipette tip and the second surface of the card.

D26. The device of embodiment D25, wherein each pipette tip support rib is in contact with the distal region of a pipette tip.

D27. The device of embodiment D25 or D26, wherein each pipette tip support rib is in contact with two pipette tips.

D28. The device of embodiment D25 or D26, wherein each pipette tip support rib is in contact with one pipette tip and no other pipette tip.

D29. The device of any one of embodiments D25 to D28, wherein the pipette tip support rib is in contact with a sealing member extending from the second surface of the card.

D30. The device of any one of embodiments D1 to D29, including a plurality of bores, each of which bores having an opening on the first surface of the card located at the intersection of four adjacent apertures, and which bores extend through at least a portion of the thickness of the card.

D31. The device of embodiment D30, wherein the bores extend through the entire thickness of the card.

D32. The device of embodiment D30 or D31, wherein the opening of each of the bores is substantially square shaped or diamond shaped.

D33. The device of embodiment D32, wherein each side of the square shaped or diamond shaped opening is a curved side.

D34. The device of embodiment D33, wherein each aperture of the card is circular and the radius of curvature of each curved side of each bore is greater than, and substantially follows, the radius of curvature of the circular aperture.

D35. The device of any one of embodiments D1 to D34, wherein the first surface is substantially flat and includes no protrusions and no sealing members.

D36. The device of embodiment D35, wherein the first surface includes no depressions.

D37. The device of embodiment D35, wherein the first surface includes depressions, each depression surrounding one aperture of the card and concentric with the aperture of the card.

E1. An integrated pipette tip device, including:
a substantially flat card including a first surface and an opposing second surface, which card includes a plurality of apertures, each aperture defining the opening of a channel traversing the thickness of the card;
which card includes a plurality of integrated pipette tips, each of which pipette tips including a distal region that effectively extends from the second surface of the card and is concentric with one aperture; and
which card includes a plurality of pipette tip support ribs, each of which pipette tip support ribs is in connection with one pipette tip and the second surface of the card.

E2. The device of embodiment E1, wherein the thickness of the card between the first surface and the second surface is about 0.5 to about 5 millimeters.

E3. The device of embodiment E1 or E2, wherein the first surface of the card includes one or more depressions, each of with depressions surrounds one aperture of the card, and each of which depressions is concentric with the aperture.

E4. The device of any one of embodiments E1 to E3, wherein the first surface of the card includes one or more protrusions, each of with protrusions surrounds one aperture of the card, and each of which protrusions is concentric with the aperture.

E5. The device of embodiment E4, wherein the protrusion includes a protrusion surface parallel to the first surface of the card, which protrusion surrounds a depression depressed from the protrusion surface, which depression surrounds one of the apertures of the card, and which protrusion is concentric with the depression and the aperture.

E6. The device of any one of embodiments E3 to E5, which includes a plurality of depressions or a plurality of protrusions, or a plurality of depressions and a plurality of protrusions.

E7. The device of embodiment E6, wherein each aperture of the card is effectively surrounded by one depression or one protrusion, or one depression and one protrusion.

E8. The device of any one of embodiments E3 to E7, wherein the protrusions are annular protrusions.

E9. The device of any one of embodiments E3 to E8, wherein the depressions are annular depressions.

E10. The device of any one of embodiments E1 to E9, wherein the distal regions of the pipette tips are in connection with the second surface.

E11. The device of any one of embodiments E1 to E10, further including a plurality of dispenser sealing members, each of which dispenser sealing members including an opening in effective association with one channel of the card.

E12. The device of embodiment E11, wherein the sealing member extends from the second surface of the card and the distal region of each pipette tip extends from the sealing member.

E13. The device of embodiment E11, wherein the sealing member is connected to the first surface of the card.

E14. The device of embodiment E11, wherein the sealing member is connected to or is seated in a protrusion surface.

E15. The device of embodiment E11, wherein the sealing member is connected to or is seated in a depression.

E16. The device of any one of embodiments E13 to E15, wherein each sealing member includes a flange surrounding the outer perimeter of the sealing member.

E17. The device of any one of embodiments E11 to E16, wherein the exterior surface of the sealing member includes no sealing member ribs, no sealing member depressions, sealing member ribs, sealing member depressions or a combination thereof.

E18. The device of embodiment E17, wherein the sealing member includes no sealing member ribs and no sealing member depressions.

E19. The device of embodiment E17, wherein the sealing member ribs or sealing member depressions are parallel to an axis extending from the aperture of the card to the distal region of the pipette tip.

E20. The device of embodiment E17 or E19, wherein the sealing member ribs include first ribs and second ribs, which first ribs and second ribs alternate along the circumference of the exterior surface of the sealing member, which first ribs are of a first thickness and which second ribs are of a second thickness, and which first thickness is different than the second thickness.

E21. The device of any one of embodiments E17, E19 and E20, wherein the sealing member includes sealing member ribs, sealing member depressions or a combination thereof, and wherein one or more of the ribs or depressions contact the flange.

E22. The device of any one of embodiments E11 to E21, wherein the sealing member is an annular sealing member.

E23. The device of any one of embodiments E11 to E22, wherein the sealing member includes an exterior wall that is substantially vertical to the first surface of the card or the second surface of the card.

E24. The device of any one of embodiments E11 to E23, wherein the sealing member includes a flexible material not present in the card or in the pipette tips.

E25. The device of any one of embodiments E11 to E23, wherein the sealing member contains the same material as the card and the pipette tips.

E26. The device of any one of embodiments E1 to E25, wherein each pipette tip support rib is in contact with the distal region of a pipette tip.

E27. The device of any one of embodiments E1 to E26, wherein each pipette tip support rib is in contact with two pipette tips.

E28. The device of any one of embodiments E1 to E26, wherein each pipette tip support rib is in contact with one pipette tip and no other pipette tip.

E29. The device of any one of embodiments E1 to E28, wherein the pipette tip support rib is in contact with a sealing member extending from the second surface of the card.

E30. The device of any one of embodiments E1 to E29, including a plurality of bores, each of which bores having an opening on the first surface of the card located at the intersection of four adjacent apertures, and which bores extend through at least a portion of the thickness of the card.

E31. The device of any one of embodiments E1 to E30, wherein the bores extend through the entire thickness of the card.

E32. The device of any one of embodiments E1 to E31, wherein the opening of each of the bores is substantially square shaped or diamond shaped.

E33. The device of embodiment E32, wherein each side of the square shaped or diamond shaped opening is a curved side.

E34. The device of embodiment E33, wherein each aperture of the card is circular and the radius of curvature of each curved side of each bore is greater than, and substantially follows, the radius of curvature of the circular aperture.

E35. The device of any one of embodiments E1 to E34, wherein the first surface is substantially flat and includes no protrusions and no sealing members.

E36. The device of embodiment E35, wherein the first surface includes no depressions.

E37. The device of embodiment E35, wherein the first surface includes depressions, each depression surrounding one aperture of the card.

E38. The device of any one of embodiments C1 to C37, D1 to D37 or E1 to E37, wherein the device includes 384 or more integrated pipette tips.

E39. The device of embodiment A38, wherein the device includes 1536 integrated pipette tips.

E40. The device of any one of embodiments C1 to C37, D1 to D37 or E1 to E39, wherein the card and pipette tips include a moldable plastic.

E41. The device of embodiment D40, wherein the plastic includes one or more of polypropylene (PP), polyethylene (PE), high-density polyethylene, low-density polyethylene, polyethylene teraphthalate (PET), polyvinyl chloride (PVC), polyethylenefluoroethylene (PEFE), polystyrene (PS), high-density polystyrene, acrylnitrile butadiene styrene copolymers, or a combination of two or more of the foregoing.

E42. The device of embodiment E41, wherein the plastic includes PE.

F1. A device of any one of embodiments C1 to C37, D1 to D37 or E1 to E42 in sealing connection with a gasket, which gasket includes apertures concentrically aligned with the apertures in the device, which gasket is relatively more resilient than the card of the device, and the surface of the gasket in connection with the first surface of the card covers about 80% or more of the first surface of the card.

F2. The device of embodiment F1, wherein the gasket includes annular gasket protrusions surrounding the gasket apertures.

F3. The device of embodiment F2, wherein each gasket protrusions is configured to sealingly engage an inner surface of one card aperture.

F4. The device of embodiment F2, wherein the card includes annular card depressions surrounding the card apertures, which card depressions are concentric with the card apertures and each of which card depressions is configured to sealingly engage with one gasket protrusion.

F5. The device of embodiment F1, wherein the card includes annular card protrusions extending from the first surface, which card protrusions surround the card apertures and are concentric with the card apertures.

F6. The device of embodiment F5, wherein each of the card protrusions is configured to sealingly engage with an inner surface of one gasket aperture.

F7. The device of embodiment F5, wherein the gasket includes annular gasket depressions surrounding the gasket apertures, which gasket depressions are concentric with the gasket apertures and each of which gasket depressions is configured to sealingly engage with one card protrusion.

F8. The device of any one of embodiments F1 to F7, wherein the surface of the gasket in connection with the first surface of the card covers about 90% or more of the first surface of the card.

F9. The device of embodiment F6, wherein the surface of the gasket in connection with the first surface of the card covers about 95% or more of the first surface of the card.

F10. The device of embodiment F9, wherein the surface of the gasket in connection with the first surface of the card covers about 100% or more of the first surface of the card.

F11. The device of any one of embodiments F1 to F10, wherein the gasket includes a moldable thermoplastic elastomer.

F12. The device of any one of embodiments F1 to F11, wherein the gasket is substantially flat.

G1. A method for dispensing a fluid by an integrated pipette tip device, including:
engaging a dispensing device with a device of any one of embodiments C1 to C37, D1 to D37, E1 to E42, and F1 to F12, drawing a fluid into the pipette tips of the integrated pipette tip device, and dispensing the fluid from the pipette tips.

G2. The method of embodiment G1, which includes ejecting the integrated pipette tip device after the fluid is ejected from the pipette tips.

H1. A mold for manufacturing an integrated pipette tip device of any one of embodiments C1 to C37, D1 to D37, or E1 to E42.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Modifications may be made to the foregoing without departing from the basic aspects of the technology. Although the technology has been described in substantial detail with reference to one or more specific embodiments, those of ordinary skill in the art will recognize that changes may be made to the embodiments specifically disclosed in this application, yet these modifications and improvements are within the scope and spirit of the technology.

The technology illustratively described herein suitably may be practiced in the absence of any element(s) not specifically disclosed herein. Thus, for example, in each instance herein any of the terms "including," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the claimed technology. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" is about 1, about 2 and about 3). For example, a weight of "about 100 grams" can include weights between 90 grams and 110 grams. Ranges presented herein include intermediate values (e.g., a range of between 80% to 90% includes basis for about 86%, for example). Thus, it should be understood that although the present technology has been specifically disclosed by representative embodiments and optional features, modification and variation of the concepts herein disclosed may be resorted to by those skilled in the art, and such modifications and variations are considered within the scope of this technology.

Embodiments of the technology are set forth in the claim(s) that follow(s).

What is claimed is:

1. An integrated pipette tip device, comprising:
a substantially flat card comprising a first surface and an opposing second surface, which card comprises a plurality of apertures, each aperture defining the opening of a channel traversing the thickness of the card;
which card comprises a plurality of pipette tips integrated with and connected to the card, each of which pipette tips comprising a distal region that effectively extends from the second surface of the card and is concentric with one aperture;
which card comprises a plurality of bores, each of which bores having an opening on the first surface of the card located at the intersection of four adjacent apertures, and which bores extend through at least a portion of the thickness of the card and about one third of the card thickness in the bore is removed; and
a plurality of pipette tip support ribs, each of which pipette tip support ribs is in contact with the distal region of a pipette tip and the second surface of the card.

2. The device of claim 1, further comprising a plurality of dispenser sealing members, each of which dispenser sealing members comprising an opening in effective association with one channel of the card.

3. The device of claim 2, wherein each of the sealing members comprises a flange surrounding the outer perimeter of the sealing member.

4. The device of claim 2, wherein the exterior surface of each of the sealing member comprises no sealing member ribs, no sealing member depressions, sealing member ribs, sealing member depressions or a combination thereof.

5. The device of claim 2, wherein each of the sealing members comprises a wall that is substantially vertical to the first surface of the card or the second surface of the card.

6. The device of claim 2, wherein each of the sealing members comprises a flexible material not present in the card or in the pipette tips.

7. The device of claim 2, wherein each of the sealing members contains the same material as the card and the pipette tips.

8. The device of embodiment 1, wherein each pipette tip support rib is in contact with two pipette tips.

9. The device of embodiment 1, wherein each pipette tip support rib is in contact with one pipette tip and no other pipette tip.

10. The device of claim 1, wherein each pipette tip support rib is in contact with a sealing member extending from the second surface of the card.

11. The device of claim 1, wherein the opening of each of the bores is substantially square shaped or substantially diamond shaped.

12. The device of claim 11, wherein each side of the substantially square shaped opening or substantially diamond shaped opening is a curved side.

13. The device of claim 12, wherein each aperture of the card is circular and the radius of curvature of each curved side of each bore is greater than, and substantially follows, the radius of curvature of the circular aperture.

14. The device of claim 1, wherein the first surface is substantially flat and comprises no protrusions and no sealing members.

15. The device of claim 1, wherein each pipette tip support rib extends from the second surface of the card to about one quarter of the length of the distal portion of each pipette tip.

16. The device of claim 1, wherein the card and pipette tips are molded with one another.

17. The device of claim 1, wherein the thickness of the card between the first surface and the second surface is about 0.5 to about 5 millimeters.

18. The device of claim 17, wherein the thickness of the card between the first surface and the second surface is about 0.5 to about 0.9 millimeters.

* * * * *